US011076594B2

(12) United States Patent
Lian et al.

(10) Patent No.: US 11,076,594 B2
(45) Date of Patent: Aug. 3, 2021

(54) PYRAZOLONE COMPOUND OR SALT THEREOF, PREPARATION METHOD THEREFOR, HERBICIDE COMPOSITION AND USE THEREOF

(71) Applicant: QINGDAO KINGAGROOT CHEMICAL COMPOUNDS CO., LTD., Shandong (CN)

(72) Inventors: Lei Lian, Shandong (CN); Yurong Zheng, Shandong (CN); Bin He, Shandong (CN); Xuegang Peng, Shandong (CN); Tao Jin, Shandong (CN); Qi Cui, Shandong (CN)

(*) Notice: Subject to any disclaimer, the term of this patent is extended or adjusted under 35 U.S.C. 154(b) by 77 days.

(21) Appl. No.: 15/559,614

(22) PCT Filed: Jan. 8, 2016

(86) PCT No.: PCT/CN2016/070453
§ 371 (c)(1),
(2) Date: Sep. 19, 2017

(87) PCT Pub. No.: WO2017/075910
PCT Pub. Date: May 11, 2017

(65) Prior Publication Data
US 2018/0055054 A1    Mar. 1, 2018

(30) Foreign Application Priority Data
Nov. 6, 2015   (CN) .......................... 201510750677.1

(51) Int. Cl.
*A01N 43/56* (2006.01)
*C07D 231/20* (2006.01)
(Continued)

(52) U.S. Cl.
CPC ............. *A01N 43/56* (2013.01); *A01N 43/60* (2013.01); *A01N 43/84* (2013.01); *A01N 47/06* (2013.01); *C07D 231/20* (2013.01); *C07D 401/10* (2013.01); *C07D 401/14* (2013.01); *C07D 403/10* (2013.01); *C07D 403/14* (2013.01); *C07D 413/10* (2013.01); (Continued)

(58) Field of Classification Search
CPC ........ A01N 43/56; A01N 43/60; A01N 43/84; A01N 47/06; C07D 231/20; C07D 401/10; C07D 401/14; C07D 403/10; C07D 403/14; C07D 413/10; C07D 413/14; C07D 417/10; C07D 417/14
USPC ........................................................ 504/219
See application file for complete search history.

(56) References Cited
U.S. PATENT DOCUMENTS 4,414,392 A    11/1983  Konotsune et al.
4,557,753 A *  12/1985  Tanaka .................. A01N 43/56
                                                    504/282
(Continued)

FOREIGN PATENT DOCUMENTS

CN        88101455 A      9/1988
CN        1036202 A      10/1989
(Continued)

OTHER PUBLICATIONS

EP Supplementary European Search Report for EP 16 86 1183 dated Sep. 21, 2018.
Office Action from corresponding RU 2018110258/04(015907) dated Dec. 5, 2018 (English translator attached).
Search Report from corresponding RU 2018110258/04(015907) dated Apr. 12, 2018 (English translation attached).
International Search Report from Chinese Application 2015107506771 dated Jun. 23, 2016.
(Continued)

*Primary Examiner* — Johann R Richter
*Assistant Examiner* — Courtney A Brown
(74) *Attorney, Agent, or Firm* — Abelman, Frayne & Schwab; Stefan Knirr

(57) ABSTRACT

The present invention belongs to the field of pesticides, particularly relates to a pyrazolone compound or a salt thereof, a preparation method therefor, a herbicidal composition and use thereof. The pyrazolone compound is as described in formula I:

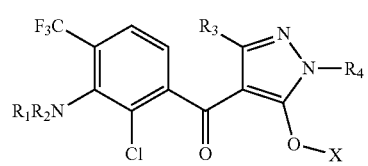

In the formula, $R_1R_2N$ represents substituted or unsubstituted 3-8 membered nitrogen-containing heterocyclic group containing 1-3 heteroatoms; or $R_1$ and $R_2$ each represent hydrogen or $C_{1-8}$ alkyl; $R_3$ represents hydrogen, $C_{1-4}$ alkyl, alkenyl, alkynyl, unsubstituted $C_{3-6}$ cycloalkyl or $C_{3-6}$ cycloalkyl substituted by $C_{1-4}$ alkyl; $R_4$ represents methyl, ethyl, n-propyl, isopropyl or cyclopropyl; X represents hydrogen, $-S(O)_nR^6$, $-R^7$ or substituted or unsubstituted 3-8 membered heterocyclic group containing 1-4 heteroatoms, wherein, n represents 1, 2 or 3, $R^6$ represents substituted or unsubstituted alkyl or aryl, and $R^7$ represents substituted or unsubstituted alkyl, aryl, alkyl acyl or aroyl. The active substance of the invention exhibits good herbicidal effect, and is convenient to use, low in cost and has great commercial value.

19 Claims, No Drawings

(51) Int. Cl.
*C07D 403/10* (2006.01)
*A01N 43/60* (2006.01)
*A01N 43/84* (2006.01)
*A01N 47/06* (2006.01)
*C07D 401/10* (2006.01)
*C07D 401/14* (2006.01)
*C07D 403/14* (2006.01)
*C07D 413/10* (2006.01)
*C07D 413/14* (2006.01)
*C07D 417/10* (2006.01)
*C07D 417/14* (2006.01)

(52) U.S. Cl.
CPC ......... *C07D 413/14* (2013.01); *C07D 417/10* (2013.01); *C07D 417/14* (2013.01)

(56) References Cited

U.S. PATENT DOCUMENTS

| | | | |
|---|---|---|---|
| 4,948,887 A | | 8/1990 | Baba et al. |
| 5,846,907 A | * | 12/1998 | von Deyn .............. A01N 43/56 504/221 |
| 6,746,989 B1 | | 6/2004 | Muller et al. |
| 7,189,679 B2 | | 3/2007 | Schmitt et al. |
| 7,279,444 B2 | | 10/2007 | Muller et al. |
| 8,030,498 B2 | | 10/2011 | Shimoharada et al. |
| 2014/0371067 A1 | * | 12/2014 | Mitchell .............. A01N 43/713 504/103 |

FOREIGN PATENT DOCUMENTS

| | | |
|---|---|---|
| CN | 1175951 A | 3/1998 |
| CN | 1938277 A | 3/2007 |
| CN | 101331119 A | 12/2008 |
| CN | 103980202 A | 8/2014 |
| CN | 105218449 A | 1/2016 |
| EA | 199700194 A1 | 2/1998 |
| GB | 2215333 A | 9/1989 |
| WO | 96/26206 A1 | 8/1996 |
| WO | 97/41106 A1 | 11/1997 |
| WO | 9746530 | 12/1997 |
| WO | 9746530 A1 | 12/1997 |
| WO | WO-9746530 A1 * | 12/1997 ........... C07D 231/12 |
| WO | 0058306 | 10/2000 |

OTHER PUBLICATIONS

International Search Report of PCT/CN2016/070453 dated Jul. 20, 2016.
Office Action of CN Patent Application No. 201510750677.1 dated Jul. 5, 2016.

* cited by examiner

PYRAZOLONE COMPOUND OR SALT THEREOF, PREPARATION METHOD THEREFOR, HERBICIDE COMPOSITION AND USE THEREOF

RELATED APPLICATION

This application is a national phase of international Application No. PCT/CN20161070453 filed Jan. 8, 2016, and claims priority from Chinese Patent Application No, 201510750677.1 filed Nov. 6, 2015, both incorporated by reference in their entirety.

TECHNICAL FIELD

The present invention belongs to the field of pesticides, particularly relates to a pyrazolone compound or a salt thereof, a preparation method therefor, a herbicidal composition and use thereof.

BACKGROUND TECHNOLOGY

There exist more than 30,000 kinds of weeds in the world, wherein about 1,800 kinds of weeds can cause great economic losses. According to statistics, the potential crops yield loses 12% in average every year in the world due to weed infestation (even though the crops have been treated with hand or mechanical weeding). Hand or mechanical weeding consumes large labor forces and energy resources, but still leads to unsatisfactory effects; the weed infestation cannot be solved completely until the application of chemical weed control methods. Chemical weed control methods are convenient, economical and effective, thus have been an indispensable part of modern agricultural technology, and also promoted the innovation of cultivation technology. In addition, herbicides are widely used in weed control of non-agricultural lands, such as forests, grasslands, urban green areas, industrial sites, roadsides (railways, highways or airports), banks, dams and ponds, etc. Therefore, developing efficient, safe and economical pesticide herbicides is one of the most important missions for guaranteeing agricultural production.

The pyrazolone compounds are characterized by high efficacy, low toxicity and variety of structures, and are mainly used as herbicides. Most of the commercialized pyrazolone herbicides are hydroxyphenylpyruvate dioxygenase (HPPD) inhibitors. They are widely used due to the systemic translocation and low toxicity to mammals, etc. Among the pyrazolone herbicides, 4-pyrazolone compounds, such as pyrazolynate, pyrazoxyfen, benzofenap and wheat herbicide pyrasulfotole, etc., are compounds in which the pyrazole ring are substituted at the 4-position by multi-substituted benzoyl groups.

Patents such as WO9741106, JP56061362, WO2002094792 and WO2008125214 have disclosed a series of pyrazolone herbicides and the preparation methods thereof. In order to design and synthesize more efficient herbicides with broader activity spectrum, on the basis of studies on the pyrazolone herbicides, the present invention synthesizes a class of novel pyrazolone compounds with herbicidal activities.

CONTENTS OF THE INVENTION

The object of the present invention is to provide a pyrazolone compound and a salt thereof, preparation method therefor, a herbicidal composition and herbicidal use in pesticide field. The compound provided in the present invention has a good efficacy, is easy to use and of low cost.

To achieve the above mentioned object, the present invention provides the following technical solution:

A pyrazolone compound as shown in formula I, or a salt thereof:

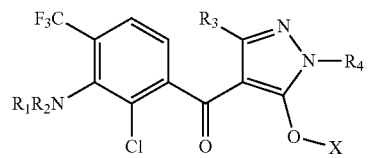

wherein, $R_1R_2N$ represents substituted or unsubstituted 3-8 membered nitrogen-containing heterocyclic group containing 1-3 heteroatoms; preferably, $R_1R_2N$ represents pyrazolyl substituted by halogen, alkyl or alkoxyl, or substituted or unsubstituted 4-8 membered lactam group containing 0-2 atoms selected from O, S and N; more preferably, $R_1R_2N$ represents a group selected from butyrolactam group

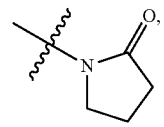 [SMILES: *N1CCCC1=O]

valerolactam group

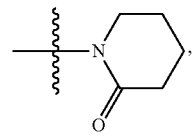 [SMILES: *N1CCCCC1=O]

caprolactam group

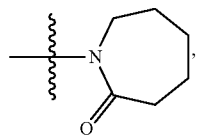 [SMILES: *N1CCCCCC1=O]

oenantholactam group

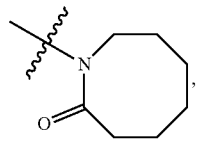 [SMILES: *N1CCCCCCC1=O]

piperazinone group

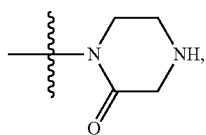 [SMILES: *N1CCNCC1=O]

morpholinone group

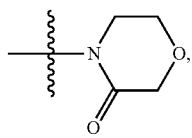 [SMILES: *N1CCOCC1=O]

thiomorpholinone group

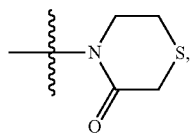 [SMILES: *N1CCSCC1=O]

imidazole group

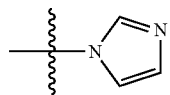 [SMILES: *n1ccnc1]

and pyrazolyl

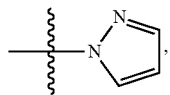

each of which is unsubstituted or substituted on ring by one or more groups selected from fluorine, chlorine, methyl, ethyl, methoxyl and ethoxyl; or,
$R_1$ and $R_2$ each represent hydrogen, $C_{1-8}$ alkyl, substituted alkyl containing 1-4 heteroatoms, alkenyl, alkynyl, substituted or unsubstituted $C_{1-4}$ acyl, unsubstituted $C_{3-6}$ cycloalkyl or $C_{3-6}$ cycloalkyl substituted by $C_{1-4}$ alkyl; preferably, one of $R_1$ and $R_2$ represents $C_{1-4}$ acyl containing O, S or N, which is unsubstituted or substituted with halogen, and the other one represents hydrogen, $C_{1-8}$ alkyl, substituted alkyl (such as $C_{1-8}$ alkyl) containing 1-4 heteroatoms, alkenyl, alkynyl, unsubstituted $C_{3-6}$ cycloalkyl or $C_{3-6}$ cycloalkyl substituted by $C_{1-4}$ alkyl; more preferably, $R_1$ represents acetyl, fluoroacetyl, difluoroacetyl, trifluoroacetyl, methoxy acetyl, ethoxy acetyl, methoxy propionyl or ethoxy propionyl, and $R_2$ represents hydrogen or a group selected from methyl, ethyl, propyl, butyl, pentyl and cyclopropyl, each of which is unsubstituted or substituted by one or more groups selected from fluorine, methoxyl, ethyoxyl, propoxy, butoxy and methoxyethoxy;
$R_3$ represents hydrogen, $C_{1-4}$ alkyl, alkenyl, alkynyl, unsubstituted $C_{3-6}$ cycloalkyl or $C_{3-6}$ cycloalkyl substituted by $C_{1-4}$ alkyl; preferably, $R_3$ represents hydrogen, methyl, ethyl or cyclopropyl;

$R_4$ represents methyl, ethyl, n-propyl, isopropyl or cyclopropyl; preferably, $R_4$ represents methyl, ethyl or isopropyl; X represents hydrogen, $—S(O)_nR^6$, $—R^7$, or substituted or unsubstituted 3-8 membered heterocyclic group containing 1-4 heteroatoms, wherein, n represents 1, 2 or 3, $R^6$ represents substituted or unsubstituted alkyl or aryl, $R^7$ represents substituted or unsubstituted alkyl, aryl, alkyl acyl or aroyl; preferably, X represents hydrogen, $—SO_2R$ or $—(C=O)R^8$, wherein, $R^6$ represents substituted or unsubstituted alkyl or aryl, $R^8$ represents alkoxy, aryloxy, substituted or unsubstituted alkyl or aryl, or substituted or unsubstituted 3-8 membered heterocyclic group containing 1-4 heteroatoms (for example, N-alkylpyrazole group

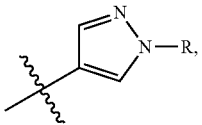

which is unsubstituted or substituted on ring by one or more groups selected from methyl, ethyl, methoxyl or ethoxyl.)

The terms "heterocycle" or "heterocyclic group" refer to 3-10 membered aromatic or non-aromatic heterocyclic ring containing 1-4 heteroatoms selected from O, N and S, or 4-10 membered ring compound having a structure of lactone, cyclic ether or lactam. Bicyclic groups are also within the terms. Hence "heterocyclic group" contains "heteroaromatic group" and dihydro analogues and tetrahydro analogues thereof. The heterocyclic substituents could be linked through carbon atoms or heteroatoms. The term "heteroaromatic group" refers to a stable monocyclic or bicyclic group that has up to 7 atoms in each ring, wherein the heteroaromatic group may comprise an aromatic ring containing 1-4 heteroatoms selected from O, N and S. The heteroaromatic group within the definition includes but is not limited to: acridinyl, carbazolyl, cinnolinyl, quinoxalinyl, pyrazolyl, indolyl, benzotriazolyl, thienyl, furyl, benzothienyl, benzofuryl, quinolyl, isoquinolyl, oxazolyl, isoxazolyl, indolyl, pyrazinyl, pyridazinyl, pyridyl, pyrimidyl, pyrryl and tetrahydroquinolyl. Similar to the definition of the heterocyclic group, "heteroaromatic group" should also be understood as including all the N-oxide derivatives of any nitrogen-containing heteroaromatic group.

The salt refers to an agriculturally acceptable salt, preferably an acid addition salt prepared by reacting the compound of the invention with a chemically acceptable acid, or a salt prepared by reacting a hydroxyl pyrazole compound having an acidic group with an alkali compound. Wherein, the acid is preferably selected from inorganic acids (such as hydrochloric acid, sulfuric acid, phosphoric acid or hydrobromic acid, etc.) and organic acids (such as oxalic acid, maleic acid, fumaric acid, malic acid, tartaric acid, citric acid or benzoic acid, etc.); the alkali compound is preferably selected from sodium hydroxide, potassium hydroxide, calcium hydroxide, sodium carbonate, potassium carbonate, sodium bicarbonate and potassium bicarbonate, etc. The above described agriculturally accepted salt is easy to be separated and can be purified by conventional methods, such as solvent extraction, dilution, recrystallization, column chromatography and thin-layer chromatography preparation, etc.

Also disclosed is a method for preparing the pyrazolone compound or the salt thereof, which comprises the following steps:

(1) a compound of formula II is reacted with an excessive amount of compound $R_1R_2NH$ to prepare a compound of formula III;
(2) the compound of formula III is reacted with compound X-A to obtain the compound of formula I;
wherein A represents halogen, methylsulfonyl or p-tosyl, and the reaction route is as follows:

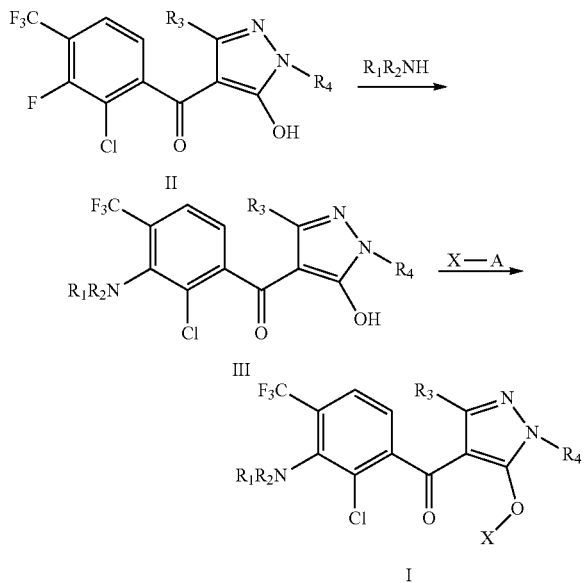

The step (1) and (2) are conducted in an aprotic solvent in the presence of a base; at a reaction temperature of $-30°$ C.-$180°$ C., preferably $-5°$ C.-$90°$ C.

The solvent is acetonitrile, diethyl ether, tetrahydrofuran, DMF or DMSO, preferably acetonitrile, tetrahydrofuran or DMF; the base is sodium hydroxide, potassium hydroxide, calcium hydroxide, sodium carbonate, potassium carbonate, sodium bicarbonate, potassium bicarbonate, triethylamine, DIPEA or DBU, preferably NaH, triethylamine or potassium carbonate.

Also disclosed is a herbicidal composition which comprises a herbicidally effective amount of at least one pyrazolone compound or the salt thereof.

The herbicidal composition also comprises a preparation auxiliary.

Also disclosed is a method for controlling a harmful plant, which comprises a step of applying a herbicidally effective amount of at least one pyrazolone compound or the salt thereof or the herbicidal composition to the plant or an area with the harmful plant.

Use of at least one pyrazolone compound or the salt thereof or the herbicidal composition in controlling a harmful plant, preferably, the pyrazolone compound or the salt thereof is applied to control the harmful plant in a desirable crop, preferably, the desirable crop is a genetically modified crop or a crop treated by a genome editing technique.

The compounds of the formula I according to the invention have an outstanding herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is generally Immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being a restriction to certain species. Examples of weed species on which the active compounds act efficiently are, from amongst the monocotyledons, *Avena*, *Lolium*, *Alopecurus*, *Phalaris*, *Echinochloa*, *Digitaria*, *Setaria* and also *Cyperus* species from the annual sector and from amongst the perennial species *Agropyron*, *Cynodon*, *Imperata* and *Sorghum*, and also perennial *Cyperus* species.

In the case of the dicotyledonous weed species, the spectrum of action extends to species such as, for example, *Galium*, *Viola*, *Veronica*, *Lamium*, *Stellaria*, *Amaranthus*, *Sinapis*, *Ipomoea*, *Sida*, *Matricaria* and *Abutilon* from amongst the annuals, and *Convolvulus*, *Cirsium*, *Rumex* and *Artemisia* in the case of the perennial weeds. The active compounds according to the invention also effect outstanding control of harmful plants which occur under the specific conditions of rice growing such as, for example, *Echinochloa*, *Sagittaria*, *Alisma*, *Eleocharis*, *Scirpus* and *Cyperus*. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. In particular, the compounds according to the invention exhibit excellent activity against *Apera spica venti*, *Chenopodium album*, *Lamium purpureum*, *Polygonum convulvulus*, *Stellaria media*, *Veronica hederifolia*, *Veronica persica*, *Viola tricolor* and against *Amaranthus*, *Galium* and *Kochia* species.

Although the compounds according to the invention have an excellent herbicidal activity against monocotyledonous and dicotyledonous weeds, crop plants of economically important crops such as, for example, wheat, barley, rye, rice, corn, sugarbeet, cotton and soya, are not damaged at all, or only to a negligible extent. In particular, they have excellent compatibility in cereals, such as wheat, barley and corn, in particular wheat. For these reasons, the present compounds are highly suitable for selectively controlling undesired plant growth in plantings for agricultural use or in plantings of ornamentals.

Owing to their herbicidal properties, these active compounds can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested produce are known.

The use of the compounds of the formula I according to the invention or their salts in economically important transgenic crops of useful and ornamental plants, for example of cereal, such as wheat, barley, rye, oats, millet, rice, maniok and corn, or else in crops of sugarbeet, cotton, soya, rapeseed, potato, tomato, pea and other vegetable species is preferred. The compounds of the formula I can preferably be used as herbicides in crops of useful plants which are resistant or which have been made resistant by genetic engineering toward the phytotoxic effects of the herbicides.

Conventional ways for preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of
genetically engineered changes in crop plants in order to modify the starch synthesized in the plants (for example WO 92/11376, WO 92/14827, WO 91/19806),
transgenic crop plants which are resistant to certain herbicides of the glufosinate- (cf., for example, EP-A 0 242 236, EP-A 0 242 246) or glyphosate-type (WO 92/00377), or of the sulfonylurea-type (EP-A 0 257 993, U.S. Pat. No. 5,013,659),
transgenic crop plants, for example cotton, having the ability to produce *Bacillus thuringiensis* toxins (Bt toxins) which impart resistance to certain pests to the plants (EP-A 0 142 924, EP-A 0 193 259),
transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim, 2nd edition 1996, or Christou, "Trends in Plant Science" 1 (1996) 423-431). In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to whole plants using known techniques.

The transgenic plants can in principle be plants of any desired plant species, i.e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants. The invention therefore also provides for the use of the compounds according to the invention as herbicides for controlling harmful plants in transgenic crop plants.

In addition, the substances according to the invention have outstanding growth-regulating properties in crop plants. They engage in the plant metabolism in a regulating manner and can this be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledon and dicotyledon crops because lodging can be reduced hereby, or prevented completely.

The compounds according to the invention can be applied in the customary formulations in the form of wettable powders, emulsifiable concentrates, sprayable solutions, dusts or granules. The invention therefore also provides herbicidal compositions comprising compounds of the formula I. The compounds of the formula I can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, dusts (DP), capsule suspensions (CS), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes. These individual formulation types are known in principle and are described, for example, in Winnacker-Kuhler, "Chemische Technologie" [Chemical Technology], Volume 7, C. Hauser Verlag Munich, 4th. Edition 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzfichenaktive thylenoxidaddukte" [Surface-active ethylene oxide adducts], Wiss. Verlagsgesell., Stuttgart 1976; Winnacker-Kuchler, "Chemische Technologie" [Chemical Technology], Volume 7, C. Hauser Verlag Munich, 4th Edition 1986.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane-6,6'-disulfonate, sodium dibutyinaphthalenesulfonate or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth. Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers. Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57. For further details on the formulation of crop protection products, see for example G. C. Klingman, "Weed Control as a Science", John Wiley and Sons Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations generally contain from 0.1 to 99% by weight, in particular from 0.1 to 95% by weight, of active compound of the formula I. In wettable powders the concentration of active compound is, for example, from about 10 to 90% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, said formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Suitable active compounds which can be combined with the active compounds according to the invention in mixed formulations or in a tank mix are, for example, known active compounds as described in for example *World Herbicide New Product Technology Handbook*, China Agricultural Science and Farming Techniques Press, 2010.9 and in the literature cited therein. For example the following active compounds may be mentioned as herbicides which can be combined with the compounds of the formula I (note: the compounds are either named by the "common name" in accordance with the International Organization for Standardization (ISO) or by the chemical names, if appropriate together with a customary code number): acetochlor, butachlor, alachlor, propisochlor, metolachlor, s-metolachlor, pretilachlor, propachlor, ethachlor, napropamide, R-left handed napropamide, propanil, mefenacet, diphenamid, diflufenican, ethaprochlor, beflubutamid, bromobutide, dimethenamid, dimethenamid-P, etobenzanid, flufenacet, thenylchlor, metazachlor, isoxaben, flamprop-M-methyl, flamprop-M-propyl, allidochlor, pethoxamid, chloranocryl, cyprazine, mefluidide, monalide, delachlor, prynachlor, terbuchlor, xylachlor, dimethachlor, cisanilide, trimexachlor, clomeprop, propyzamide, pentanochlor, carbetamide, benzoylprop-ethyl, cyprazole, butenachlor, tebutam, benzipram, 1379, dichiofluanid, naproanilide, diethatyl-ethyl, naptalam, flufenacet, benzadox, chlorthiamid, chlorophthalimide, isocarbamide, picolinafen, atrazine, simazine, prometryn, cyanatryn, simetryn, ametryn, propazine, dipropetryn, SSH-108, terbutryn, terbuthylazine, triaziflam, cyprazine, proglinazine, trietazine, prometon, simetone, aziprotryne, desmetryn, dimethametryn, procyazine, mesoprazine, sebuthylazine, secbumeton, terbumeton, methoprotryne, cyanatryn, ipazine, chlorazine, atraton, pendimethalin, eglinazine, cyanuric acid, indaziflam, chlorsulfuron, metsulfuron-methyl, bensulfuron methyl, chlorimuron-ethyl, tribenuron-methyl, thifensulfuron-methyl, pyrazosulfuron-ethyl, mesosulfuron, iodosulfuron-methyl sodium, foramsulfuron, cinosulfuron, triasulfuron, sulfometuron methyl, nicosulfuron, ethametsulfuron-methyl, amidosulfuron, ethoxysulfuron, cyclosulfamuron, rimsulfuron, azimsulfuron, flazasulfuron, monosulfuron, monosulfuron-ester, flucarbazone-sodium, flupyrsulfuron-methyl, halosulfuron-methyl, oxasulfuron, imazosulfuron, primisulfuron, propoxycarbazone, prosulfuron, sulfosulfuron, trifloxysulfuron, triflusulfuron-methyl, tritosulfuron, sodium metsulfuron methyl, flucetosulfuron, HNPC-C, orthosulfamuron, propyrisulfuron, metazosulfuron, acifluorfen, fomesafen, lactofen, fluoroglycofen, oxyfluorfen, chlomitrofen, aclonifen, ethoxyfen-ethyl, bifenox, nitrofluorfen, chlomethoxyfen, fluorodifen, fluoronitrofen, furyloxyfen, nitrofen, TOPE, DMNP, PPG1013, AKH-7088, halosafen, chlortoluron, isoproturon, linuron, diuron, dymron, fluometuron, benzthiazuron, methabenzthiazuron, cumyluron, ethidimuron, isouron, tebuthiuron, buturon, chlorbromuron, methyldymron, phenobenzuron, SK-85, metobromuron, metoxuron, afesin, monuron, siduron, fenuron, fluothiuron, neburon, chloroxuron, noruron, isonoruron, 3-cydooctyl-1, thiazfluron, tebuthiuron, difenoxuron, parafluron, methylamine tribunil, karbutilate, trimeturon, dimefuron, monisouron, anisuron, methiuron, chloreturon, tetrafluron, phenmedipham, phenmedipham-ethyl, desmedipham, asulam, terbucarb, barban, propham, chlorpropham, rowmate, swep, chlorbufam, carboxazole, chlorprocarb, fenasulam, BCPC, CPPC, carbasulam, butylate, benthiocarb, vernolate, molinate, triallate, dimepiperate, esprocarb, pyributicarb, cycloate, avadex, EPTC, ethiolate, orbencarb, pebulate, prosulfocarb, tiocarbazil, CDEC, dimexano, isopolinate, methiobencarb, 2,4-D butyl ester, MCPA-Na, 2,4-D isooctyl ester, MCPA isooctyl ester, 2,4-D sodium salt, 2,4-D dimethylamine salt, MCPA-thioethyl, MCPA, 2,4-D propionic acid, high 2,4-D propionic acid salt, 2,4-D butyric acid, MCPA propionic acid, MCPA propionic acid salt, MCPA butyric acid, 2,4,5-D, 2,4,5-D propionic acid, 2,4,5-D butyric acid, MCPA amine salt, dicamba, erbon, chlorfenac, saison, TBA, chloramben, methoxy-TBA, diclofop-methyl, fluazifop-butyl, fluazifop-p-butyl, haloxyfop-methyl, haloxyfop-P, quizalofop-ethyl, quizalofop-p-ethyl, fenoxaprop-ethy, fenoxaprop-p-ethyl, propaquizafop, cyhalofop-butyl, metamifop, clodinafop-propargyl, fenthiaprop-ethyl, chloroazifop-propynyl, poppenate-methyl, trifopsime, isoxapyrifop, paraquat, diquat, oryzalin, ethalfluralin, isopropalin, nitralin, profluralin, prodinamine, benfluralin, fluchloraline, dinitramina, dipropalin, chlomidine, methalpropalin, dinoprop, glyphosate, anilofos, glufosinate ammonium, amiprophos-methyl, sulphosate, piperophos, bialaphos-sodium, bensulide, butamifos, phocarb, 2,4-DEP, H-9201, zytron, imazapyr, imazethapyr, imazaquin, imazamox, imazamox ammonium salt, imazapic, imazamethabenz-methyl, fluroxypyr, fluroxypyr isooctyl ester, dopyralid, picloram, trichlopyr, dithiopyr, haloxydine, 3,5,6-trichloro-2-pyridinol, thiazopyr, fluridone, aminopyralid, diflufenzopyr, triclopyr-butotyl, Cliodinate, sethoxydim, clethodim, cycloxydim, alloxydim, clefoxydim, butroxydim, tralkoxydim, tepraloxydim, buthidazole, metribuzin, hexazinone, metamitron, ethiozin, ametridione, amibuzin, bromoxynil, bromoxynil octanoate, ioxynil octanoate, loxynil, dichlobenil, diphenatrile, pyracionil, chloroxynil, iodobonil, flumetsulam, florasulam, penoxsulam, metosulam, cloransulam-methyl, diclosulam, pyroxsulam, benfuresate, bispyribac-sodium, pyribenzoxim, pyriftalid, pyriminobac-methyl, pyrithiobac-sodium, benzobicylon, mesotrione, sulcotrione, tembotrione, tefuryltrione, bicyclopyrone, ketodpiradox, isoxaflutole, clomazone, fenoxasulfone, methiozolin, fluazolate, pyraflufen-ethyl, pyrazolynate, difenzoquat, pyrazoxyfen, benzofenap, nipyraclofen, pyrasulfotole, topramezone, pyroxasulfone, cafenstrole, flupoxam, aminotriazole, amicarbazone, azafenidin, carfentrazone-ethyl, sulfentrazone, bencarbazone, benzfendizone, butafenacil, bromacil, isocil, lenacil, terbacil, flupropacil, cinidon-ethyl, flumidorac-pentyl, flumioxazin, propyzamide, MK-129, flumezin, pentachlorophenol, dinoseb, dinoterb, dinoterb acetate, dinosam, DNOC, chloronitrophene, medinoterb acetate, dinofenate, oxadiargyl, oxadiazon, pentoxazone, Flufenacet, fluthiacet-methyl, fentrazamide, flufenpyr-ethyl, pyrazon, brompyrazon, metflurazon, kusakira, dimidazon, oxapyrazon, norflurazon, pyridafol, quinclorac, quinmerac, bentazone, pyridate, oxaziclomefone, benazolin, clomazone, cinmethylin, ZJ0702, pyribambenz-propyl, indanofan, sodium chlorate, dalapon, trichloroacetic acid, monochloroacetic acid, hexachloroacetone, flupropanate, cyperquat, bromofenoxim, epronaz, methazole, flurtamone, benfuresate, ethofumesate, tiodorim, chlorthal, fluorochioridone, tavron, acrolein, bentranil, tridiphane, chlorfenpropmethyl, thidiarizonaimin, phenisopham, busoxinone, methoxyphenone, saflufenadl, clacyfos, chloropon, alorac, diethamquat, etnipromid, iprymidam, ipfencarbazone, thiencarbazone-methyl, pyrimisulfan, chlorflurazole, tripropindan, sulglycapin, prosulfalin, cambendichlor, aminocydopyrachlor, rodethanil, benoxacor, fendorim, flurazole, fenchlorazole-ethyl, cloquintocet-mexyl, oxabetrinil, MG/91, cyometrinil, DKA-24, mefenpyr-diethyl, furilazole, fluxofenim, isoxadifen-ethyl, dichiormid, halauxifen-methyl, DOW848, UBH-509, D489, LS 82-556, KPP-300, NC-324, NC-330, KH-218, DPX-N8189, SC-0744, DOWC0535, DK-8910, V-53482, PP-600, MBH-001, KIH-9201, ET-751, KIH-6127 and KIH-2023.

For use, the formulations which are presented in commercially available form are, if appropriate, diluted in the customary manner, for example using water in the case of wettable powders, emulsifiable concentrates, dispersions and water-dispersible granules. Products in the form of dusts, granules for soil application or broadcasting and sprayable solutions are usually not further diluted with other inert substances prior to use. The application rate of the compounds of the formula I required varies with the external conditions, such as temperature, humidity, the nature of the herbicide used and the like. It can vary within wide limits, for example between 0.001 and 1.0 kg/ha or more of active substance, but it is preferably between 0.005 and 750 g/ha, in particular between 0.005 and 250 g/ha.

Specific Mode for Carrying Out the Invention

The following embodiments are used to illustrate the present invention in detail and should not be taken as any limit to the present invention. The scope of the invention would be explained through the Claims.

The method for preparing the compound of the invention will be explained in detail in the following program and embodiment. The material is commercial available or prepared through known method reported in the literature or shown in the route. Those skilled in the art should understand that the compound of the invention can also be synthesized by other synthetic route. Although the detailed material and reaction condition in the synthetic route have been explicated in the following text, it is still easy to be replaced by other similar material and condition. Isomer of the compound, for example, that produced with the variation of the preparation method of the present invention is included in the scope of the present invention. In addition, the following preparation method can be further modified according to the disclosures of the present invention by using common chemical method known to those skilled in the art. For example, protect suitable group in the process of the reaction, etc.

In view of economic and variety of the compound, the following method of application can be used to improve further understanding of the preparation method of the present invention. The specific material, class and condition have been determined to be further explication of the present invention, not to be any limit of the reasonable scope thereof. Reagents of the following synthetic compound showed in the table can either be purchased from the market or easily prepared by those skilled in the art. Wherein the condition of $^1$HNMR is as follows: $^1$H-NMR is determined by AVANCE AV-500 Nuclear Magnetic Resonance (NMR), TMS is the internal standard. The mass spectrum is determined by Shimadzu-2010A mass spectrometer.

Exemplary embodiment for preparation of the intermediate (A-1-4);

1. Synthesis of (2-chloro-3-fluoro-4-trifluoromethylphenyl)-(5-hydroxy-1-methyl-1H-pyrazol-4-yl)-methanone (A-1)

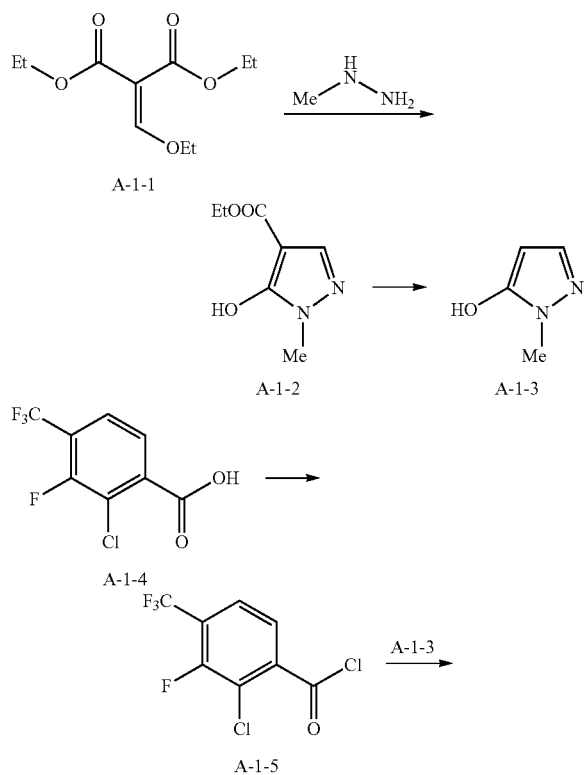

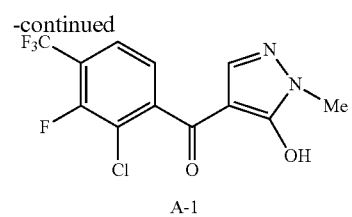

115 g of 40% methylhydrazine solution was mixed with 400 ml of water, and cooled to 0~5° C., then slowly dropped in with 216 g of Diethyl ethoxymethylenemalonate (A-1-1) with stirring. The reaction mixture was refluxed for 6 hours after the addition, and then cooled to room temperature (RT) to precipitate large amount of solid. The crude product was collected by sucking filtration. The obtained crude product was recrystallized with ethanol to obtain 75 g of white solid (A-1-2) with 44.1% yield and 97.02% HPLC purity. 22 g of NaOH was dissolved in 300 ml of water, and added with 42.5 g of intermediate (A-1-2) with stirring. The mixture was stirred for 3 hours at 40° C., then cooled to RT and added with 55 ml of concentrated hydrochloric acid, and then heated to reflux and reacted for 3 hours. The solvent was removed by evaporation. The residue was added into 200 ml of absolute ethyl alcohol and stirred thoroughly. The insoluble substance was removed by filtration. The filtrate was concentrated under reduced pressure to give 24 g of off-white solid (A-1-3) with 98.0% yield and 96.50% HPLC purity.

5.1 g of 2-chloro-3-fluoro-4-trifluoromethylbenzoic acid (A-1-4) was mixed with 10 ml of thionyl chloride, the mixture was stirred at reflux for 1 hour, and then evaporated to remove excessive thionyl chloride to obtain 5.5 g of 2-chloro-3-fluorine-4-trifluoromethylphenylformyl chloride (A-1-5) as a light yellow liquid with yield of 100%. The product was used in next reaction directly without purification.

9 ml of triethylamine and 2.5 g of 2-methyl-2H-pyrazol-3-ol (A-1-3) were dissolved in 30 ml of 1,2-dichloroethane, and cooled to −5° C. A solution of 5.5 g of 2-chloro-3-fluoro-4-trifluoromethylbenzoyl chloride (A-1-5) prepared above in 20 ml of 1,2-dichloroethane was added dropwise, the temperature was controlled to no higher than 5° C. After the addition, the reaction mixture was stirred at RT overnight. To the reaction mixture was added diluted hydrochloric acid to adjust pH to 2~3. The organic phase was separated, washed successively with water and saturated sodium chloride solution, dried and concentrated to obtain 6 g of yellow solid (A-1) with 86.9% yield and 95.10% HPLC purity.

2. The Synthesis of (2-chloro-3-fluoro-4-trifluoromethylphenyl)-(5-hydroxy-1,3-dimethyl-1H-pyrazol-4-yl)-methanone (A-2)

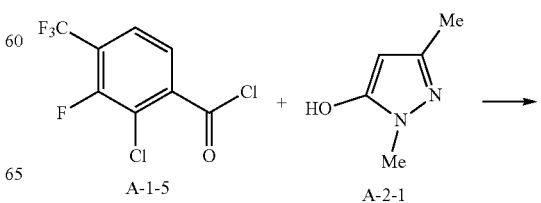

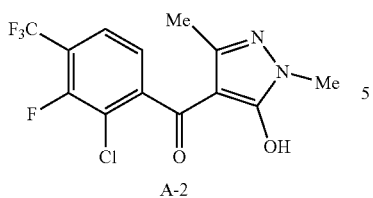

A-2

9 ml of triethylamine and 2.4 g of 2,5-dimethyl-2H-pyrazol-3-ol (A-2-1) were dissolved in 20 ml of 1,2-dichloroethane, and cooled to −5° C. A solution of 5.2 g of 2-chloro-3-fluoro-4-trifluoromethylbenzoyl chloride (A-1-5) prepared above in 5 ml of 1,2-dichloroethane were added dropwise. The temperature was controlled to no higher than 5° C. After the addition, the reaction solution was stirred at RT for 2 hours. 1 ml of acetone cyanohydrin was added into the reaction solution, heated to 50~60° C. and stirred overnight. The reaction was cooled to RT., diluted hydrochloric acid was added to adjust pH to 2~3, then separated. The organic phase was washed successively with water and saturated sodium chloride solution, dried and concentrated to obtain 4.3 g of yellow solid (A-2) with 63.7% yield and 98.28% HPLC purity.

3. The Synthesis of (2-chloro-3-fluoro-4-trifluoromethylphenyl)-(5-hydroxy-1-methyl-3-cyclopropyl-1H-pyrazol-4-yl)-methanone (A-3)

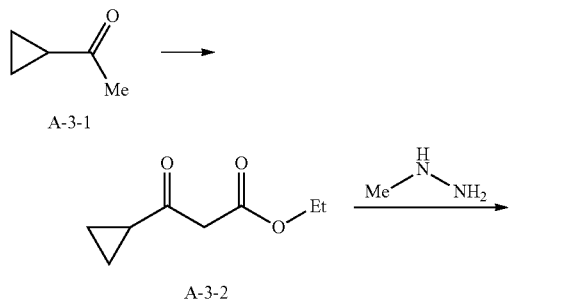

48 g of sodium tert-butoxide was added into 500 ml of toluene, cooled to 10° C., and added dropwise with 225 g of dimethyl carbonate. 75.7 g cyclopropyl ethanone was added dropwise after stirring for 30 minutes. The temperature of the reaction was controlled to no higher than 15° C. The reaction solution was stirred for a further 30 min after the addition, then heated to 75° C. and reacted overnight. The reaction solution was poured into 500 ml of ice water after cooling to RT, hydrochloric acid was used to adjust pH to 1~2. The obtained mixture was separated, the organic phase was washed successively with water and saturated sodium chloride solution, dried and concentrated to obtain 83 g of orange grease (A-3-2) with 60% yield and 93% purity.

115 g of 40% methylhydrazine solution and 140 g of intermediate (A-3-2) were mixed with 500 ml of ethyl alcohol. The mixture was stirred and reflux for 4 hours and then cooled to RT. The volatilizable substances were evaporated by decompression. The residue was recrystallized in alcohol-acetic acid to to obtain 50 g of yellow solid (A-3-3) with yield of 40.2% and HPLC purity of 95%.

10 g of triethylamine and 9.3 g of 2-methyl-5-cyclopropyl pyrazol-2H-3-ol (A-3-3) were dissolved in 50 ml of 1,2-dichloroethane and cooled to −5° C. A solution of 16.1 g of 2-chloro-3-fluoro-4-trifluoromethylbenzoyl chloride (A-1-5) prepared above in 25 ml of 1,2-dichloroethane was added dropwise, the temperature was controlled to no higher than 5° C. After the addition, the solution was stirred at RT for 2 hours. 9 g of triethylamine and 1 ml of acetone cyanohydrins were added, then heated to 50~60° C. and stirred overnight. The reaction solution was cooled to RT., hydrochloric acid was added to adjust pH to 2~3 and separated. The organic phase was washed successively with water and saturated sodium chloride solution, dried and concentrated to obtain 20 g of yellow solid (A-3) with 89.2% yield and 99.30% HPLC purity.

4. The synthesis of 1-methyl-5-ethyoxyl-pyrazole-4-formic acid (A-4)

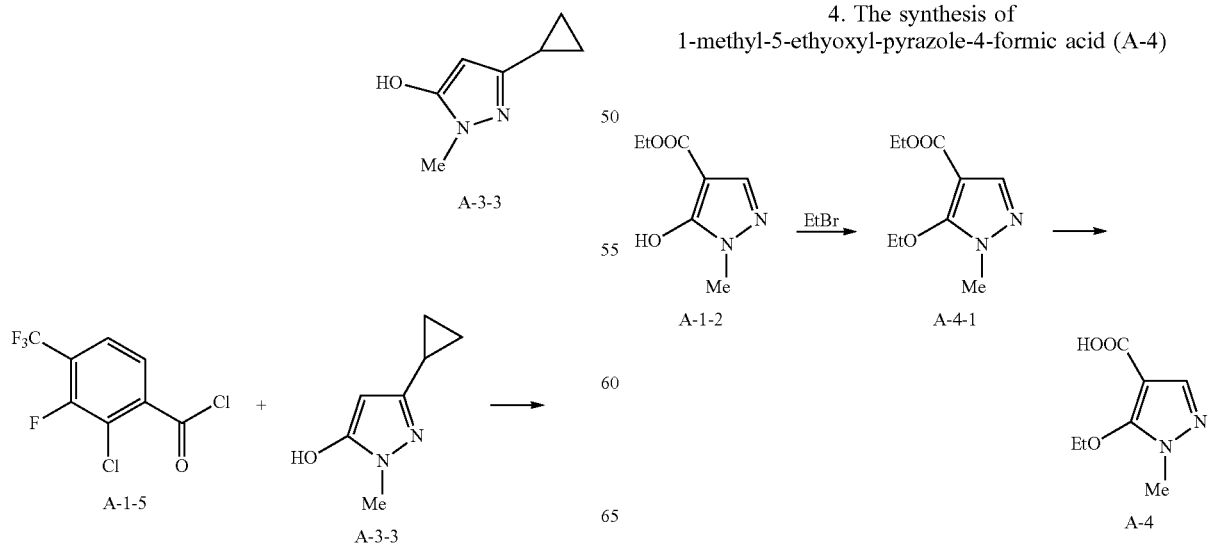

17 g of 1-methyl-5-hydroxyl-pyrazole-4-ethyl formate (A-1-2) was dissolved in 150 ml of DMF. 13.8 g of anhydrous potassium carbonate was added under stirring and then 16.5 g of bromoethane was added dropwise. After the addition, the reaction solution was stirred overnight. The reaction solution was poured into 1.5 L of water and stirred thoroughly, then extracted with ethyl acetate. The organic phase was washed with water and saturated sodium chloride solution successively, dried and concentrated under reduced pressure to obtain 19.8 g of orange grease (A-4-1) with the yield of 100%. The product was used directly to the next step of reaction without purification.

8 g of NaOH was dissolved in 50 ml of water. 19 g of 1-methyl-5-ethyoxyl-pyrazole-4-ethyl formate (A-4-1) was added slowly at RT. The reaction solution was stirred overnight at RT, and then 3N hydrochloric acid was added to adjust pH to 2~3. Ethyl acetate was added into the solution and extracted. The organic phase was washed with water and saturated sodium chloride solution successively, dried and concentrated to obtain 13 g of white solid (A-4) with the yield of 79.7% and HPLC purity of 95.3%.

Preparation of Target Compounds of the Invention:

The following table presents a series of compounds with the following structure prepared according to the methods of the present invention, using the compounds prepared via the above mentioned methods as raw material.

I

| compound ID | $R_1R_2N$ = | $R_3$ = | $R_4$ = | X = | HNMR |
|---|---|---|---|---|---|
| 001 | —NH$_2$ | Me | Me | H | [DMSO-d$_6$, 500 MHz] δ 7.41 (d, J = 8.0 Hz, 1H), 6.56 (d, J = 8.0 Hz, 1H), 3.38 (s, 3H), 2.06 (s, 3H). |
| 002 | —NH—C(O)Me | Me | Me | H | [DMSO-d$_6$, 500 MHz] δ 9.87 (s, 1H), 7.77 (d, J = 8.5 Hz, 1H), 7.45 (d, J = 7.5 Hz, 1H), 3.38 (s, 3H), 2.05 (s 6H). |
| 003 | —NH—C(O)CHF$_2$ | Me | Me | H | [DMSO-d$_6$, 500 MHz] δ 7.79 (d, J = 8.5 Hz, 1H), 7.48 (d, J = 7.5 Hz, 1H), 6.25 (s, 1H), 3.48 (s, 3H), 2.18 (s 3H). |
| 004 | —N(Ac)(Me) | Me | Me | H | [DMSO-d$_6$, 500 MHz] δ 7.77 (d, J = 8.5 Hz, 1H), 7.45 (d, J = 7.5 Hz, 1H), 3.46 (s, 3H), 3.38 (s, 3H), 2.02 (s 6H). |
| 005 | —N(C(O)Me)(CH$_2$CHF$_2$) | Me | Me | H | [DMSO-d$_6$, 500 MHz] δ 7.74 (d, J = 7.5 Hz, 1H), 7.56 (d, J = 7.5 Hz, 1H), 6.39 (t, J = 54.0 Hz, 1H), 4.71-4.22 (m, 2H), 3.53 (s, 3H), 2.25 (s, 3H), 2.02 (s, 3H). |
| 006 | —N(C(O)Me)(CH$_2$CH$_2$CH$_2$Me) | Me | Me | H | [DMSO-d$_6$, 500 MHz] δ 7.76 (d, J = 7.5 Hz, 1H), 7.44 (d, J = 7.5 Hz, 1H), 4.44-4.39 (m, 2H), 3.55 (s, 3H), 2.42 (s, 3H), 2.06 (s, 3H), 1.45-0.91 (m, 7H). |
| 007 | —N(C(O)Me)(CH$_2$CH$_2$OMe) | Me | Me | H | [DMSO-d$_6$, 500 MHz] δ 7.77 (d, J = 7.5 Hz, 1H), 7.46 (d, J = 7.5 Hz, 1H), 3.80-3.60 (m, 7H), 3.55 (s, 3H), 2.47 (s, 3H), 2.04 (s, 3H). |

-continued

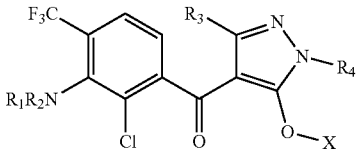

I

| compound ID | R₁R₂N = | R₃ = | R₄ = | X = | HNMR |
|---|---|---|---|---|---|
| 008 | (CH2CH2CH2OMe)) | Me | Me | H | [DMSO-d₆, 500 MHz] δ 7.75 (d, J = 7.5 Hz, 1H), 7.43 (d, J = 7.5 Hz, 1H), 4.45-4.39 (m, 2H), 3.55 (s, 3H), 3.39-3.36 (m, 2H), 3.31 (s, 3H), 2.42 (s, 3H), 2.06 (s, 3H), 1.66-1.60 (m, 2H). |
| 009 | (CH2CH2CH2OEt)) | Me | Me | H | [DMSO-d₆, 500 MHz] δ 7.75 (d, J = 7.5 Hz, 1H), 7.43 (d, J = 7.5 Hz, 1H), 4.45-4.39 (m, 2H), 3.54 (q, J = 6.5 Hz, 2H), 3.39-3.36 (m, 2H), 3.32 (s, 3H), 2.42 (s, 3H), 2.06 (s, 3H), 1.66-1.33 (m, 5H). |
| 010 | (CH2CH2CH2OiPr)) | Me | Me | H | [DMSO-d₆, 500 MHz] δ 7.75 (d, J = 7.5 Hz, 1H), 7.43 (d, J = 7.5 Hz, 1H), 4.45-4.39 (m, 2H), 3.39-3.22 (m, 6H), 2.42 (s, 3H), 2.06 (s, 3H), 1.66-1.60 (m, 2H), 1.18 (d, J = 7.0 Hz, 6H). |
| 011 | (CH2CH2CH2OBu)) | Me | Me | H | [DMSO-d₆, 500 MHz] δ 7.75 (d, J = 7.5 Hz, 1H), 7.43 (d, J = 7.5 Hz, 1H), 4.45-4.39 (m, 2H), 3.39-3.30 (m, 7H), 2.42 (s, 3H), 2.06 (s, 3H), 1.68-1.51 (m, 6H), 1.02 (t, J = 6.5 Hz, 3H). |
| 012 | (CH2CH2CH2OCH(Me)OMe)) | Me | Me | H | [DMSO-d₆, 500 MHz] δ 7.75 (d, J = 7.5 Hz, 1H), 7.43 (d, J = 7.5 Hz, 1H), 4.45-4.39 (m, 2H), 3.39-3.26 (m, 12H), 2.42 (s, 3H), 2.06 (s, 3H), 1.66-1.54 (m, 2H). |
| 013 | C(O)CH2OMe) | Me | Me | H | [DMSO-d₆, 500 MHz] δ 7.78 (d, J = 7.5 Hz, 1H), 7.45 (d, J = 7.5 Hz, 1H), 4.45 (s, 2H), 3.55 (s, 3H), 3.42 (s, 3H), 3.39 (s, 3H). |
| 014 | | H | Me | H | [DMSO-d₆ 500 MHz] δ 7.85 (d, J = 7.5 Hz, 1H), 7.69 (s, 1H), 7.55 (d, J = 7.5 Hz, 1H), 3.70-3.60 (m, 2H), 3.38 (s, 3H), 2.44 (t, J = 6.5 Hz, 2H), 2.35-2.18 (m, 2H). |
| 015 | | H | Me | C(O)-(5-EtO-1-Me-pyrazol-4-yl)) | [DMSO-d₆, 500 MHz] δ 7.95 (s, 1H), 7.85 (d, J = 7.5 Hz, 1H), 7.69 (s, 1H), 7.55 (d, J = 7.5 Hz, 1H), 4.42 (q, J = 7.0 Hz, 2H), 3.70-3.60 (m, 5H), 3.38 (s, 3H), 2.44 (t, J = 6.5 Hz, 2H), 2.38-2.20 (m, 2H), 1.35 (t, J = 7.0 Hz, 3H). |

-continued

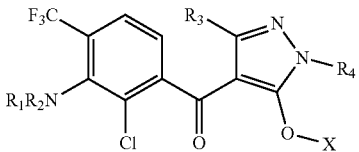

I

| compound ID | R₁R₂N = | R₃ = | R₄ = | X = | HNMR |
|---|---|---|---|---|---|
| 016 | pyrrolidinone | H | Me | 1-Me-3-Me-pyrazol-4-yl carbonyl | [DMSO-d₆, 500 MHz] δ 8.15 (s, 1H), 7.85 (d, J = 7.5 Hz, 1H), 7.69 (s, 1H), 7.55 (d, J = 7.5 Hz, 1H), 3.82 (s, 3H), 3.70-3.60 (m, 2H), 3.38 (s, 3H), 2.49 (s, 3H), 2.40 (t, J = 6.5 Hz, 2H), 2.35-2.18 (m, 2H). |
| 017 | pyrrolidinone | H | Me | 1-Me-pyrazol-4-yl carbonyl | [DMSO-d₆, 500 MHz] δ 8.33 (s, 1H), 7.85 (d, J = 7.5 Hz, 1H), 7.80 (s, 1H), 7.69 (s, 1H), 7.55 (d, J = 7.5 Hz, 1H), 3.85 (s, 3H), 3.70-3.60 (m, 2H), 3.38 (s, 3H), 2.44 (t, J = 6.5 Hz, 2H), 2.36-2.21 (m, 2H). |
| 018 | pyrrolidinone | Me | Me | H | [DMSO-d₆, 500 MHz] δ 7.85 (d, J = 7.5 Hz, 1H), 7.55 (d, J = 7.5 Hz, 1H), 3.71 (d, J = 8.0 Hz, 1H), 3.54 (s, 1H), 3.38 (s, 3H), 2.44 (t, J = 6.5 Hz, 2H), 2.35-2.20 (m, 5H). |
| 019 | pyrrolidinone | Me | Me | EtSO₂— | [DMSO-d6, 500 MHz] δ 7.85 (d, J = 7.5 Hz, 1H), 7.55 (d, J = 7.5 Hz, 1H), 3.71 (d, J = 8.0 Hz, 1H), 3.54 (s, 1H), 3.45 (q, J = 6.5 Hz, 2H), 3.38 (s, 3H), 2.44 (t, J = 6.5 Hz, 2H), 2.35-2.20 (m, 5H), 1.35 (t, J = 7.0 Hz, 3H). |
| 020 | pyrrolidinone | Me | Me | methoxycarbonyl | [DMSO-d₆, 500 MHz] δ 7.85 (d, J = 7.5 Hz, 1H), 7.55 (d, J = 7.5 Hz, 1H), 3.83 (s, 3H), 3.71 (d, J = 8.0 Hz, 1H), 3.54 (s, 1H), 3.38 (s, 3H), 2.44 (t, J = 6.5 Hz, 2H), 2.35-2.20 (m, 5H). |
| 021 | pyrrolidinone | Me | Me | 1-Me-5-EtO-pyrazol-4-yl carbonyl | [DMSO-d₆, 500 MHz] δ 8.03 (s, 1H), 7.85 (d, J = 7.5 Hz, 1H), 7.55 (d, J = 7.5 Hz, 1H), 4.40 (q, J = 7.0 Hz, 2H), 3.72-3.70 (m, 4H), 3.54 (s, 1H), 3.48 (s, 3H), 2.44 (t, J = 6.5 Hz, 2H), 2.35-2.20 (m, 5H), 1.33 (t, J = 7.0 Hz, 3H). |
| 022 | pyrrolidinone | Me | Me | 1-Me-pyrazol-4-yl carbonyl | [DMSO-d₆, 500 MHz] δ 8.33 (s, 1H), 7.89-7.80 (m, 2H), 7.55 (d, J = 7.5 Hz, 1H), 3.83 (s, 3H), 3.54-3.50 (m, 2H), 3.38 (s, 3H), 2.44 (t, J = 6.5 Hz, 2H), 2.35-2.15 (m, 5H). |

-continued

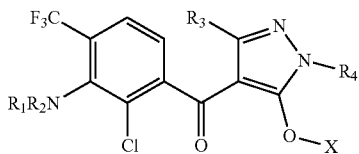

I

| compound ID | R₁R₂N = | R₃ = | R₄ = | X = | HNMR |
|---|---|---|---|---|---|
| 023 | pyrrolidinone-N | Me | Me | 1,3-dimethylpyrazole-4-carbonyl | [DMSO-d$_6$, 500 MHz] δ 8.14 (s, 1H), 7.85 (d, J = 7.5 Hz, 1H), 7.55 (d, J = 7.5 Hz, 1H), 3.80 (s, 3H), 3.71 (d, J = 8.0 Hz, 1H), 3.54 (s, 1H), 3.38 (s, 3H), 2.46-2.20 (m, 10H). |
| 024 | 5-methoxy-pyrrolidinone-N | Me | Me | H | [DMSO-d$_6$, 500 MHz] δ 7.92 (d, J = 7.5 Hz, 1H), 7.63 (d, J = 7.5 Hz, 1H), 4.99-4.86 (m, 1H), 3.58 (s, 3H), 3.46 (s, 3H), 2.56-2.01 (m, 7H). |
| 025 | pyrrolidinone-N | cyclopropyl | Me | H | [DMSO-d$_6$, 500 MHz] δ 7.83 (d, J = 7.5 Hz, 1H), 7.61 (d, J = 7.5 Hz, 1H), 3.70-3.54 (m, 2H), 3.38 (s, 3H), 2.60-2.44 (m, 3H), 2.35-2.20 (m, 2H), 1.41-0.61(m, 4H). |
| 026 | pyrrolidinone-N | cyclopropyl | Me | 5-ethoxy-1-methyl-pyrazole-4-carbonyl | [DMSO-d$_6$, 500 MHz] δ 7.88-7.80 (m, 2H), 7.61 (d, J = 7.5 Hz, 1H), 4.42 (q, J = 6.5 Hz, 2H), 3.70-3.54 (m, 5H), 3.38 (s, 3H), 2.60-2.55 (m, 2H), 2.44-2.20 (m, 3H), 1.41-0.61 (m, 4H), 1.35 (t, J = 6.5 Hz, 3H). |
| 027 | pyrrolidinone-N | cyclopropyl | Me | 1,3-dimethylpyrazole-4-carbonyl | [DMSO-d$_6$, 500 MHz] δ 8.15 (s, 1H), 7.83 (d, J = 7.5 Hz, 1H), 7.61 (d, J = 7.5 Hz, 1H), 3.80 (s, 3H), 3.70-3.54 (m, 2H), 3.38(s, 3H), 2.60-2.55 (m, 2H), 2.44 (s, 3H), 2.35-2.20 (m, 3H), 1.41-0.61 (m, 4H). |
| 028 | pyrrolidinone-N | cyclopropyl | Me | 1-methylpyrazole-4-carbonyl | [DMSO-d$_6$, 500 MHz] δ 8.33 (s, 1H), 7.85-7.82 (m, 2H), 7.61 (d, J = 7.5 Hz, 1H), 3.85 (s, 3H), 3.70-3.54 (m, 2H), 3.38 (s, 3H), 2.45-2.09 (m, 5H), 1.41-0.61 (m, 4H). |
| 029 | piperidin-2-one-N | H | Me | H | [DMSO-d$_6$, 500 MHz] δ 7.85 (d, J = 7.5 Hz, 1H), 7.69 (s, 1H), 7.55 (d, J = 7.5 Hz, 1H), 3.39-3.32 (m, 5H), 2.25-2.11 (m, 2H), 1.68-1.40 (m, 4H). |

-continued

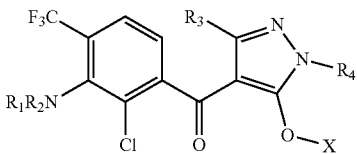

I

| compound ID | R₁R₂N = | R₃ = | R₄ = | X = | HNMR |
|---|---|---|---|---|---|
| 030 | ![piperidone] | H | Me | Ac— | [DMSO-d₆, 500 MHz] δ 7.85 (d, J = 7.5 Hz, 1H), 7.69 (s, 1H), 7.55 (d, J = 7.5 Hz, 1H), 3.39-3.32 (m, 5H), 2.25-2.06 (m, 5H), 1.68-1.40 (m, 4H). |
| 031 | ![piperidone] | H | Me | EtSO₂— | [DMSO-d₆, 500 MHz] δ 7.85 (d, J = 7.5 Hz, 1H), 7.69 (s, 1H), 7.55 (d, J = 7.5 Hz, 1H), 3.39-3.32 (m, 7H), 2.25-2.11 (m, 2H), 1.68-1.40 (m, 4H), 1.33 (t, J = 7.0 Hz, 3H). |
| 032 | ![piperidone] | H | Me | ![EtO-pyrazole-C(O)-] | [DMSO-d₆, 500 MHz] δ 7.95 (s, 1H), 7.85 (d, J = 7.5 Hz, 1H),7.69 (s, 1H), 7.55 (d, J = 7.5 Hz, 1H), 4.41 (q, J = 7.0 Hz, 2H), 3.71 (s, 3H), 3.39-3.32 (m, 5H), 2.25-2.11 (m, 2H), 1.68-1.40 (m, 4H), 1.35 (t, J = 7.0 Hz, 3H). |
| 033 | ![piperidone] | H | Me | ![pyrazole-C(O)-] | [DMSO-d₆, 500 MHz] δ 8.33 (s, 1H), 7.88-7.84 (m, 2H), 7.69 (s, 1H), 7.55 (d, J = 7.5 Hz, 1H), 3.85 (s, 3H), 3.39-3.31 (m, 5H), 2.46-2.43 (m, 2H), 1.68-1.40 (m, 4H). |
| 034 | ![piperidone] | H | Me | ![Me-pyrazole-C(O)-] | [DMSO-d₆, 500 MHz] δ 8.11 (s, 1H), 7.85 (d, J = 7.5 Hz, 1H), 7.69 (s, 1H), 7.55 (d, J = 7.5 Hz, 1H), 3.76 (s, 3H), 3.39-3.31 (m, 5H), 2.46-2.43 (m, 5H), 1.68-1.40 (m, 4H). |
| 035 | ![piperidone] | Me | Me | H | [DMSO-d₆, 500 MHz] δ 7.65 (d, J = 7.5 Hz, 1H), 7.46 (s, 1H), 3.39-3.31 (m, 5H), 2.46-2.43 (m, 5H), 1.68-1.40 (m, 4H). |
| 036 | ![piperidone] | Me | Me | ![C(O)OEt] | [DMSO-d₆, 500 MHz] δ 7.65 (d, J = 7.5 Hz, 1H), 7.46 (s, 1H), 4.35 (q, J = 7.0 Hz, 2H), 3.39-3.31 (m, 5H), 2.46-2.43 (m, 5H), 1.68-1.30 (m, 7H). |

-continued

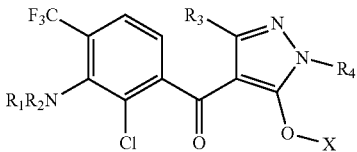

I

| compound ID | R₁R₂N = | R₃ = | R₄ = | X = | HNMR |
|---|---|---|---|---|---|
| 037 | piperidin-2-one (N-linked) | Me | Me | 1-methyl-5-ethoxy-pyrazol-4-yl carbonyl | [DMSO-d₆, 500 MHz] δ 7.98 (s, 1H), 7.65 (d, J = 7.5 Hz, 1H), 7.46 (s, 1H), 4.41 (q, J = 7.0 Hz, 2H), 3.71 (s, 3H), 3.39-3.32 (m, 8H), 2.25-2.11 (m, 2H), 1.68-1.40 (m, 4H), 1.35 (t, J = 7.0 Hz, 3H). |
| 038 | piperidin-2-one (N-linked) | Me | Me | 1,3-dimethyl-pyrazol-4-yl carbonyl | [DMSO-d₆, 500 MHz] δ 8.15 (s, 1H), 7.65 (d, J = 7.5 Hz, 1H), 7.46 (s, 1H) 3.76 (s, 3H), 3.39-3.31 (m, 8H), 2.46-2.43 (m, 5H), 1.68-1.40 (m, 4H). |
| 039 | piperidin-2-one (N-linked) | Me | Me | 1-methyl-pyrazol-4-yl carbonyl | [DMSO-d₆, 500 MHz] δ 8.33 (s, 1H), 7.85 (s, 1H), 7.65 (d, J = 7.5 Hz, 1H), 7.46 (s, 1H), 3.85 (s, 3H), 3.39-3.31 (m, 5H), 2.46-2.35 (m, 5H), 1.68-1.40 (m, 4H). |
| 040 | piperazin-2-one (N-linked) | Me | Me | H | [DMSO-d₆, 500 MHz] δ 7.66 (d, J = 7.5 Hz, 1H), 7.45 (s, 1H), 3.51-3.32 (m, 7H), 2.86-2.66 (m, 2H), 2.52 (s, 3H). |
| 041 | piperazin-2-one (N-linked) | Me | Me | 1-methyl-pyrazol-4-yl carbonyl | [DMSO-d₆, 500 MHz] δ 8.33 (s, 1H), 7.85 (s, 1H), 7.65 (d, J = 7.5 Hz, 1H), 7.46 (s, 1H), 3.88 (s, 3H), 3.53-3.30 (m, 7H), 2.90-2.66 (m, 2H), 2.50 (s, 3H). |
| 042 | morpholin-3-one (N-linked) | Me | Me | H | [DMSO-d₆, 500 MHz] δ 7.65 (d, J = 7.5 Hz, 1H), 7.45 (s, 1H), 3.66-3.32 (m, 9H), 2.55 (s, 3H). |
| 043 | morpholin-3-one (N-linked) | Me | Me | 1-methyl-pyrazol-4-yl carbonyl | [DMSO-d₆, 500 MHz] δ 8.35 (s, 1H), 7.86 (s, 1H), 7.66 (d, J = 7.5 Hz, 1H), 7.43 (s, 1H), 3.91 (s, 3H), 3.72-3.30 (m, 9H), 2.53 (s, 3H). |

-continued

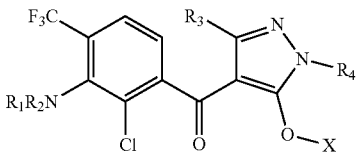

I

| compound ID | R₁R₂N = | R₃ = | R₄ = | X = | HNMR |
|---|---|---|---|---|---|
| 044 | ![N-thiomorpholinone] | Me | Me | H | [DMSO-d₆, 500 MHz] δ 7.64 (d, J = 7.5 Hz, 1H), 7.44 (s, 1H), 3.75-3.37 (m, 9H), 2.52 (s, 3H). |
| 045 | ![N-thiomorpholinone] | Me | Me | ![acyl-methylpyrazole] | [DMSO-d₆, 500 MHz] δ 8.38 (s, 1H), 7.88 (s, 1H), 7.67 (d, J = 7.5 Hz, 1H), 7.45 (s, 1H), 3.95 (s, 3H), 3.81-3.38 (m, 9H), 2.50 (s, 3H). |
| 046 | ![N-piperidinone] | ![cyclopropyl] | Me | H | [DMSO-d₆, 500 MHz] δ 7.68 (d, J = 7.5 Hz, 1H), 7.46 (s, 1H), 3.65 (s, 3H), 3.39-3.28 (m, 12H), 2.92-2.86 (m, 1H), 2.46-2.35 (m, 2H), 1.68-0.61 (m, 8H). |
| 047 | ![N-piperidinone] | ![cyclopropyl] | Me | ![acyl-methylpyrazole] | [DMSO-d₆, 500 MHz] δ 8.15 (s, 1H), 7.68 (d, J = 7.5 Hz, 1H), 7.46 (s, 1H), 3.81 (s, 3H), 3.65 (s, 3H), 3.39-3.22 (m, 2H), 2.92-2.86 (m, 1H), 2.46-2.43 (m, 5H), 1.68-0.61 (m, 8H). |
| 048 | ![N-piperidinone] | ![cyclopropyl] | Me | ![acyl-EtO-methylpyrazole] | [DMSO-d₆, 500 MHz] δ 7.96 (s, 1H), 7.68 (d, J = 7.5 Hz, 1H), 7.46 (s, 1H), 4.40 (q, J = 7.0 Hz, 2H), 3.75 (s, 3H), 3.65 (s, 3H), 3.39-3.31 (m, 2H), 2.92-2.86 (m, 1H), 2.46-2.43 (m, 2H), 1.68-0.61 (m, 11H). |
| 049 | ![N-piperidinone] | ![cyclopropyl] | Me | ![acyl-methylpyrazole] | [DMSO-d₆, 500 MHz] δ 8.33 (s, 1H), 7.85-7.68 (m, 2H), 7.46 (s, 1H), 3.85 (s, 3H), 3.65 (s,3H), 3.39-3.28 (m, 2H), 2.92-2.86 (m, 2H), 2.46-2.43 (m, 2H), 1.68-0.61 (m, 8H). |
| 050 | ![N-azepanone] | H | Me | H | [DMSO-d₆, 500 MHz] δ 7.85 (d, J = 7.5 Hz, 1H), 7.69 (s, 1H), 7.55 (d, J = 7.5 Hz, 1H), 3.60-3.52 (m, 5H), 2.25-2.01 (m, 2H), 1.68-1.40 (m, 4H), 1.35-1.24 (m, 2H). |

-continued

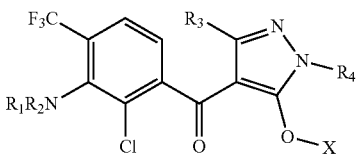

I

| compound ID | R₁R₂N = | R₃ = | R₄ = | X = | HNMR |
|---|---|---|---|---|---|
| 051 | azepan-2-one (N-linked) | H | Me | 2-(1-methyl-5-ethoxy-1H-pyrazol-4-yl)-2-oxoethyl | [DMSO-d₆, 500 MHz] δ 7.96-7.85 (m, 2H), 7.69 (s, 1H), 7.55 (d, J = 7.5 Hz, 1H), 4.45 (q, J = 7.0 Hz, 2H), 3.70 (s, 3H), 3.60-3.51 (m, 5H), 2.25-2.01 (m, 2H), 1.68-1.24 (m, 9H). |
| 052 | azepan-2-one (N-linked) | H | Me | 2-(1,3-dimethyl-1H-pyrazol-4-yl)-2-oxoethyl | [DMSO-d₆, 500 MHz] δ 8.15 (s, 1H), 7.85 (d, J = 7.5 Hz, 1H), 7.69 (s, 1H), 7.55 (d, J = 7.5 Hz, 1H), 3.81 (s, 3H), 3.60-3.55 (m, 5H), 2.45 (s, 3H), 2.25-2.01 (m, 2H), 1.68-1.22 (m, 6H), |
| 053 | azepan-2-one (N-linked) | H | Me | 2-(1-methyl-1H-pyrazol-4-yl)-2-oxoethyl | [DMSO-d₆, 500 MHz] δ 8.35 (s, 1H), 7.88-7.83 (m, 2H), 7.69 (s, 1H), 7.55 (d, J = 7.5 Hz, 1H), 3.85 (s, 3H), 3.60-3.52 (m, 5H), 2.25-2.01 (m, 2H), 1.68-1.24 (m, 6H). |
| 054 | azepan-2-one (N-linked) | Me | Me | H | [DMSO-d₆, 500 MHz] δ 7.85 (d, J = 7.5 Hz, 1H), 7.55 (d, J = 7.5 Hz, 1H), 3.60-3.50 (m, 5H), 2.36 (s, 3H), 2.25-2.01 (m, 2H), 1.68-1.24 (m, 6H). |
| 055 | azepan-2-one (N-linked) | Me | Me | ethoxycarbonylmethyl | [DMSO-d₆, 500 MHz] δ 7.85 (d, J = 7.5 Hz, 1H), 7.55 (d, J = 7.5 Hz, 1H), 4.21 (q, J = 7.0 Hz, 2H), 3.60-3.55 (m, 5H), 2.36 (s, 3H), 2.25-2.01 (m, 2H), 1.68-1.18 (m, 9H) |
| 056 | azepan-2-one (N-linked) | Me | Me | 2-(1-methyl-5-ethoxy-1H-pyrazol-4-yl)-2-oxoethyl | [DMSO-d₆, 500 MHz] δ 7.93-7.85 (m, 2H), 7.55 (d, J = 7.5 Hz, 1H), 4.42 (q, J = 7.0 Hz, 2H), 3.72 (s, 3H), 3.60-3.55 (m, 5H), 2.36 (s, 3H), 2.25-2.01 (m, 2H), 1.68-1.40 (m, 4H), 1.35-1.24 (m, 5H). |
| 057 | azepan-2-one (N-linked) | Me | Me | 2-(1-methyl-1H-pyrazol-4-yl)-2-oxoethyl | [DMSO-d₆, 500 MHz] δ 8.35 (s, 1H), 7.80-7.62 (m, 2H), 7.55 (d, J = 7.5 Hz, 1H), 3.85 (s, 3H), 3.60-3.55 (m, 5H), 2.36 (s, 3H), 2.25-2.01 (m, 2H), 1.68-1.24 (m, 6H). |

-continued

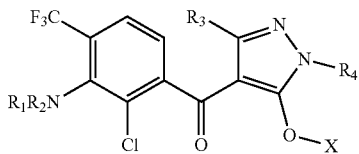

I

| compound ID | R₁R₂N = | R₃ = | R₄ = | X = | HNMR |
|---|---|---|---|---|---|
| 058 | azepan-2-one (N-linked) | Me | Me | 3-methyl-1-methyl-pyrazol-4-yl carbonyl | [DMSO-d₆, 500 MHz] δ 8.14 (s, 1H), 7.85 (d, J = 7.5 Hz, 1H), 7.55 (d, J = 7.5 Hz, 1H), 3.81 (s, 3H), 3.60-3.55 (m, 5H), 2.46 (s, 3H), 2.36 (s, 3H), 2.25-2.01(m, 2H), 1.68-1.24 (m, 6H). |
| 059 | azepan-2-one (N-linked) | cyclopropyl | Me | H | [DMSO-d₆, 500 MHz] δ 7.76 (d, J = 7.5 Hz, 1H), 7.58 (d, J = 7.5 Hz, 1H), 3.60-3.55 (m, 5H), 2.90-2.75 (m, 1H), 2.25-2.01 (m, 2H), 1.68-1.40 (m, 4H), 1.35-0.61 (m, 6H). |
| 060 | azepan-2-one (N-linked) | cyclopropyl | Me | 5-ethoxy-1-methyl-pyrazol-4-yl carbonyl | [DMSO-d₆, 500 MHz] δ 7.96 (s, 1H), 7.76 (d, J = 7.5 Hz, 1H), 7.58 (d, J = 7.5 Hz, 1H), 4.39 (q, J = 7.0 Hz, 2H), 3.72 (s, 3H), 3.60-3.55 (m, 5H), 2.90-2.75 (m, 1H), 2.25-2.01 (m, 2H), 1.68-1.40 (m, 4H), 1.35-0.61 (m, 9H). |
| 061 | azepan-2-one (N-linked) | cyclopropyl | Me | 1-methyl-pyrazol-4-yl carbonyl | [DMSO-d₆, 500 MHz] δ 8.29 (s, 1H), 7.83 (s, 1H), 7.76 (d, J = 7.5 Hz, 1H), 7.58 (d, J = 7.5 Hz, 1H), 3.82 (s, 3H), 3.60-3.55 (m, 5H), 2.90-2.75 (m, 1H), 2.25-2.01 (m, 2H), 1.68-1.40 (m, 4H), 1.35-0.61 (m, 6H). |
| 062 | azepan-2-one (N-linked) | cyclopropyl | Me | 3-methyl-1-methyl-pyrazol-4-yl carbonyl | [DMSO-d₆, 500 MHz] δ 8.13 (s, 1H), 7.76 (d, J = 7.5 Hz, 1H), 7.58 (d, J = 7.5 Hz, 1H), 3.81 (s, 3H), 3.60-3.55 (m, 5H), 2.90-2.75 (m, 1H), 2.44 (s, 3H), 2.25-2.01 (m, 2H), 1.68-1.40 (m, 4H), 1.35-0.61 (m, 6H). |
| 063 | imidazol-1-yl | Me | Me | H | [DMSO-d₆, 500 MHz] δ 7.98-7.71 (m, 3H), 7.20-7.18(m, 2H), 3.68 (s, 3H), 2.47 (s, 3H). |
| 064 | pyrazol-1-yl | H | Me | H | [DMSO-d₆, 500 MHz] δ 7.96-7.71 (m, 5H), 6.57 (s,1H), 3.72 (s, 3H). |

-continued

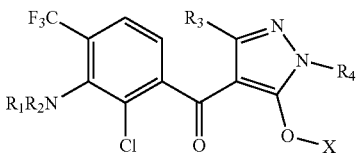

I

| compound ID | R₁R₂N = | R₃ = | R₄ = | X = | HNMR |
|---|---|---|---|---|---|
| 065 | pyrazol-1-yl | H | Me | -C(=O)-(5-EtO-1-Me-pyrazol-4-yl) | [DMSO-d$_6$, 500 MHz] δ 8.03 (s, 1H), 7.95-7.70 (m, 5H), 6.55(s, 1H), 4.40 (q, J = 7.0 Hz, 2H), 3.70 (s, 3H), 3.63 (s, 3H), 1.33 (t, J = 7.0 Hz, 3H). |
| 066 | pyrazol-1-yl | H | Me | -C(=O)-(1-Me-pyrazol-4-yl) | [DMSO-d$_6$, 500 MHz] δ 8.03 (s, 1H), 7.95-7.70 (m, 6H), 6.55(s, 1H), 3.63 (s, 3H), 2.63 (s,3H). |
| 067 | pyrazol-1-yl | H | Me | -C(=O)-(3-Me-1-Me-pyrazol-4-yl) | [DMSO-d$_6$, 500 MHz] δ 8.15 (s, 1H), 7.96-7.71 (m, 5H), 6.57 (s, 1H), 3.81 (s, 3H), 3.72 (s, 3H), 2.46 (s, 3H). |
| 068 | pyrazol-1-yl | Me | Me | H | [DMSO-d$_6$, 500 MHz] δ 7.96-7.71 (m, 4H), 6.56 (s, 1H), 3.66 (s, 3H), 2.46 (s, 3H). |
| 069 | pyrazol-1-yl | Me | Me | -C(=O)-O-Et | [DMSO-d$_6$, 500 MHz] δ 7.96-7.69 (m, 4H), 6.55 (s, 1H), 4.25 (q, J = 7.0 Hz, 2H), 3.64 (s, 3H), 2.44 (s, 3H), 1.35 (t, J = 7.0 Hz, 3H). |
| 070 | pyrazol-1-yl | Me | Me | -C(=O)-(1-Me-pyrazol-4-yl) | [DMSO-d$_6$, 500 MHz] δ 8.35 (s, 1H), 7.96-7.71 (m, 5H), 6.56 (s, 1H), 3.85 (s, 3H), 3.66 (s, 3H), 2.46 (s, 3H). |
| 071 | pyrazol-1-yl | Me | Me | -C(=O)-(5-EtO-1-Me-pyrazol-4-yl) | [DMSO-d$_6$, 500 MHz] δ 7.96-7.69 (m, 5H), 6.55 (s, 1H), 4.42 (q, J = 7.0 Hz, 2H), 3.72 (s, 3H), 3.66 (s, 3H), 2.45 (s, 3H), 1.35 (t, J = 7.0 Hz, 3H). |

-continued

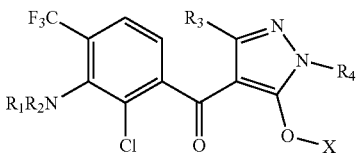

I

| compound ID | R₁R₂N = | R₃ = | R₄ = | X = | HNMR |
|---|---|---|---|---|---|
| 072 | pyrazol-1-yl | Me | Me | 1-methyl-3-methylpyrazole-4-carbonyl | [DMSO-d$_6$, 500 MHz] δ 8.15 (s, 1H), 7.96-7.71 (m, 4H), 6.54 (s, 1H), 3.82 (s, 3H), 3.65 (s, 3H), 2.46 (s, 3H), 2.40 (s, 3H). |
| 073 | pyrazol-1-yl | cyclopropyl | Me | H | [DMSO-d$_6$, 500 MHz] δ 7.92-7.63 (m, 4H), 6.58 (m, 1H), 3.58 (s, 3H), 2.72-2.58 (m, 1H), 1.42-0.65 (m, 4H). |
| 074 | pyrazol-1-yl | cyclopropyl | Me | 5-ethoxy-1-methylpyrazole-4-carbonyl | [DMSO-d$_6$, 500 MHz] δ 7.95-7.63 (m, 5H), 6.58 (m, 1H), 4.41 (q, J = 7.0 Hz, 2H), 3.72 (s, 3H), 3.58 (s, 3H), 2.72-2.58 (m, 1H), 1.42-0.65 (m, 7H). |
| 075 | pyrazol-1-yl | cyclopropyl | Me | 1,3-dimethylpyrazole-4-carbonyl | [DMSO-d$_6$, 500 MHz] δ 8.15 (s, 1H), 7.92-7.63 (m, 4H), 6.58 (m, 1H), 3.81 (s, 3H), 3.58 (s, 3H), 2.72-2.58 (m, 1H), 2.40 (s, 3H), 1.42-0.65 (m, 4H). |
| 076 | pyrazol-1-yl | cyclopropyl | Me | 1-methylpyrazole-4-carbonyl | [DMSO-d$_6$, 500 MHz] δ 8.35 (s, 1H), 7.92-7.63 (m, 5H), 6.58 (m, 1H), 3.82 (s, 3H), 3.58 (s, 3H), 2.72-2.58 (m, 1H), 1.42-0.62 (m, 4H). |
| 077 | 3-methylpyrazol-1-yl | Me | Me | H | [DMSO-d$_6$, 500 MHz] δ 7.85-7.80 (m, 2H), 7.69-7.60 (m, 1H), 6.58-6.22 (m, 1H), 3.51-3.31 (m, 3H), 2.41-2.23 (m, 6H). |
| 078 | 3-methylpyrazol-1-yl | Me | Me | ethoxycarbonyl | [DMSO-d$_6$, 500 MHz] δ 7.88-7.80 (m, 2H), 7.69-7.60 (m, 1H), 6.55-6.21 (m, 1H), 4.21-4.09 (m, 2H), 3.51-3.31 (m, 3H), 2.41-2.23 (m, 6H), 1.39-1.29 (m, 3H). |
| 079 | 3-methoxypyrazol-1-yl | Me | Me | H | [DMSO-d$_6$, 500 MHz] δ 7.89-7.81 (m, 2H), 7.71 (s, 1H), 6.35 (s, 1H), 4.18 (s, 3H), 3.51 (s, 3H), 2.44 (s, 3H). |

-continued

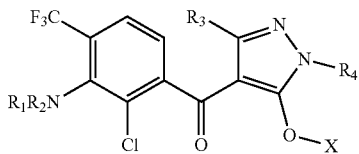

I

| compound ID | R₁R₂N = | R₃ = | R₄ = | X = | HNMR |
|---|---|---|---|---|---|
| 080 | 4-Me-pyrazol-1-yl | H | Me | H | [DMSO-d₆, 500 MHz] δ 8.03 (s, 1H), 7.95-7.55 (m, 4H), 3.63 (s, 3H), 2.11 (s, 3H). |
| 081 | 4-Me-pyrazol-1-yl | H | Me | -C(=O)-(5-EtO-1-Me-pyrazol-4-yl) | [DMSO-d₆, 500 MHz] δ 8.03 (s, 1H), 7.95-7.55 (m, 5H), 4.44 (q, J = 7.0 Hz, 2H), 3.72 (s, 3H), 3.63 (s, 3H), 2.11 (s, 3H), 1.35 (t, J = 7.0 Hz, 3H). |
| 082 | 4-Me-pyrazol-1-yl | H | Me | -C(=O)-(3-Me-1-Me-pyrazol-4-yl) | [DMSO-d₆, 500 MHz] δ 8.15 (s, 1H), 8.03 (s, 1H), 7.96-7.55 (m, 4H), 3.80 (s, 3H), 3.63 (s, 3H), 2.44 (s, 3H), 2.11 (s, 3H). |
| 083 | 4-Me-pyrazol-1-yl | H | Me | -C(=O)-(1-Me-pyrazol-4-yl) | [DMSO-d₆, 500 MHz] δ 8.35 (s, 1H), 8.05 (s, 1H), 7.98-7.51 (m, 5H), 3.85 (s, 3H), 3.61 (s, 3H), 2.10 (s, 3H). |
| 084 | 4-Me-pyrazol-1-yl | Me | Me | H | [DMSO-d₆, 500 MHz] δ 7.85-7.80 (m, 2H), 7.69-7.60 (m, 2H), 3.56 (s, 3H), 2.23 (s, 3H), 2.12 (s, 3H). |
| 085 | 4-Me-pyrazol-1-yl | Me | Me | -C(=O)-O-Et | [DMSO-d₆, 500 MHz] δ 7.85-7.80 (m, 2H), 7.70-7.61 (m, 2H), 3.82-3.56 (m, 5H), 2.25 (s, 3H), 2.13 (s, 3H), 1.28 (t, J = 7.0 Hz, 3H). |
| 086 | 4-Me-pyrazol-1-yl | Me | Me | -C(=O)-(5-EtO-1-Me-pyrazol-4-yl) | [DMSO-d6, 500 MHz] δ 7.95 (s, 1H), 7.85-7.80 (m, 2H), 7.69-7.58 (m, 2H), 4.41 (q, J = 7.0 Hz, 2H), 3.72 (s, 3H), 3.54 (s, 3H), 2.23 (s, 3H), 2.13 (s, 3H), 1.35 (t, J = 7.0 Hz, 3H). |

-continued

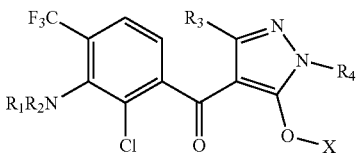

I

| compound ID | R₁R₂N = | R₃ = | R₄ = | X = | HNMR |
|---|---|---|---|---|---|
| 087 | 4-methyl-pyrazol-1-yl | Me | Me | 1-methyl-pyrazol-4-yl carbonyl | [DMSO-d₆, 500 MHz] δ 8.35 (s, 1H), 7.85-7.80 (m, 3H), 7.69-7.60 (m, 2H), 3.85 (s, 3H), 3.56 (s, 3H), 2.25 (s, 3H), 2.13 (s, 3H). |
| 088 | 4-methyl-pyrazol-1-yl | Me | Me | 1,3-dimethyl-pyrazol-4-yl carbonyl | [DMSO-d₆, 500 MHz] δ 8.15 (s, 1H), 7.86-7.78 (m, 2H), 7.69-7.58 (m, 2H), 3.81 (s, 3H), 3.56 (s, 3H), 2.45 (s, 3H), 2.22 (s, 3H), 2.12 (s, 3H). |
| 089 | 4-methyl-pyrazol-1-yl | cyclopropyl | Me | H | [DMSO-d₆, 500 MHz] δ 7.81-7.63 (m, 3H), 7.58 (s, 1H), 3.58 (s, 3H), 2.92-2.58 (m, 1H), 2.13 (s, 3H), 1.42-0.65 (m, 4H). |
| 090 | 4-methyl-pyrazol-1-yl | cyclopropyl | Me | 1,3-dimethyl-pyrazol-4-yl carbonyl | [DMSO-d₆, 500 MHz] δ 8.13 (s, 1H), 7.81-7.63 (m, 3H), 7.58 (s, 1H), 3.81 (s, 3H), 3.58 (s, 3H), 2.92-2.58 (m, 1H), 2.44 (s, 3H), 2.15 (s, 3H), 1.44-0.60 (m, 4H). |
| 091 | 4-methyl-pyrazol-1-yl | cyclopropyl | Me | 1-methyl-pyrazol-4-yl carbonyl | [DMSO-d₆, 500 MHz] δ 8.32 (s, 1H), 7.84 (s, 1H), 7.80-7.62 (m, 3H), 7.55 (s, 1H), 3.83 (s, 3H), 3.53 (s, 3H), 2.90-2.55 (m, 1H), 2.11 (s, 3H), 1.40-0.60 (m, 4H). |
| 092 | 4-methyl-pyrazol-1-yl | cyclopropyl | Me | 5-ethoxy-1-methyl-pyrazol-4-yl carbonyl | [DMSO-d₆, 500 MHz] δ 7.95 (s, 1H), 7.81-7.63 (m, 3H), 7.58 (s, 1H), 4.40 (q, J = 7.0 Hz, 2H), 3.71 (s, 3H), 3.58 (s, 3H), 2.92-2.58 (m, 1H), 2.14 (s, 3H), 1.45-0.62 (m, 7H). |
| 093 | 3,5-dimethyl-pyrazol-1-yl | Me | Me | H | [DMSO-d₆, 500 MHz] δ 7.85 (d, J = 8.0 Hz, 1H), 7.71 (d, J = 7.5 Hz, 1H), 6.21 (s, 1H), 3.58 (s, 3H), 2.46 (s, 3H), 2.28 (s, 3H), 1.96 (s, 3H). |

-continued

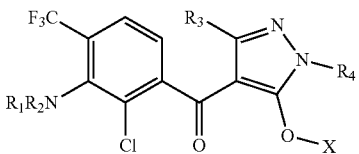

I

| compound ID | R₁R₂N = | R₃ = | R₄ = | X = | HNMR |
|---|---|---|---|---|---|
| 094 | ![3,5-dimethylpyrazol-1-yl] | Me | Me | ![1,3-dimethylpyrazol-4-yl carbonyl] | [DMSO-d₆, 500 MHz] δ 8.12 (s, 1H), 7.81 (d, J = 8.0 Hz, 1H), 7.69 (d, J = 7.5 Hz, 1H), 6.09 (s, 1H), 3.79 (s, 3H), 3.56 (s, 3H), 2.42 (s, 3H), 2.23 (s, 6H), 1.86 (s, 3H). |
| 095 | ![4-chloropyrazol-1-yl] | Me | Me | H | [DMSO-d₆, 500 MHz] δ 7.98 (s, 1H), 7.79 (s, 1H), 7.82 (d, J = 7.5 Hz, 1H), 7.65 (d, J = 7.5 Hz, 1H), 3.38 (s, 3H), 2.85 (s, 3H). |
| 096 | ![2-oxopyrrolidin-1-yl] | H | Et | H | [DMSO-d₆, 500 MHz] δ 7.88 (d, J = 7.5 Hz, 1H), 7.72 (s, 1H), 7.59 (d, J = 7.5 Hz, 1H), 3.99 (q, J = 6.5 Hz, 2H), 3.80-3.69 (m, 2H), 2.44-2.21 (m, 4H), 1.41 (t, J = 6.5 Hz, 3H). |
| 097 | ![2-oxopyrrolidin-1-yl] | H | Et | ![1,3-dimethylpyrazol-4-yl carbonyl] | [DMSO-d₆, 500 MHz] δ 8.18 (s, 1H), 7.89 (d, J = 7.5 Hz, 1H), 7.71 (s, 1H), 7.56 (d, J = 7.5 Hz, 1H), 4.03 (q, J = 6.5 Hz, 2H), 3.88 (s, 3H), 3.73-3.60 (m, 2H), 2.47 (s, 3H), 2.41 (t, J = 6.5 Hz, 2H), 2.35-2.18 (m, 2H), 1.39 (t, J = 6.5 Hz, 3H). |
| 098 | ![2-oxopyrrolidin-1-yl] | Me | Et | H | [DMSO-d₆, 500 MHz] δ 7.85 (d, J = 7.5 Hz, 1H), 7.55 (d, J = 7.5 Hz, 1H), 3.99 (q, J = 6.5 Hz, 2H), 3.71 (d, J = 8.0 Hz, 1H), 3.54 (s, 1H), 2.44 (t, J = 6.5 Hz, 2H), 2.35-2.20 (m, 5H), 1.40 (t, J = 6.5 Hz, 3H), |
| 099 | ![2-oxopyrrolidin-1-yl] | Me | Et | ![1,3-dimethylpyrazol-4-yl carbonyl] | [DMSO-d6, 500 MHz] δ 8.18 (s, 1H), 7.86 (d, J = 7.5 Hz, 1H), 7.56 (d, J = 7.5 Hz, 1H), 4.12-3.94 (m, 5H), 3.74 (d, J = 8.0 Hz, 1H), 3.56 (s, 1H), 2.48-2.18 (m, 10H), 1.36 (t, J = 6.5 Hz, 3H). |
| 100 | ![2-oxopyrrolidin-1-yl] | Et | Me | H | [DMSO-d6, 500 MHz] δ 7.90 (d, J = 7.5 Hz, 1H), 7.61 (d, J = 7.5 Hz, 1H), 3.78-3.42 (m, 5H), 3.21 (q, J = 6.5 Hz, 2H), 2.38-2.10 (m, 4H), 1.31 (t, J = 6.5 Hz, 3H). |

-continued

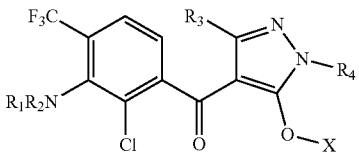

I

| compound ID | R₁R₂N = | R₃ = | R₄ = | X = | HNMR |
|---|---|---|---|---|---|
| 101 | pyrrolidinone | Et | Me | 1-methyl-3-methyl-pyrazole-4-carbonyl | [DMSO-d6, 500 MHz] δ 8.19 (s, 1H), 7.91 (d, J = 7.5 Hz, 1H), 7.60 (d, J = 7.5 Hz, 1H), 3.95 (s, 3H), 3.78-3.42, (m, 5H), 3.21 (q, J = 6.5 Hz, 2H), 2.50 (s, 3H), 2.38-2.10 (m, 4H), 1.31 (t, J = 6.5 Hz, 3H). |
| 102 | pyrrolidinone | Et | Et | H | [DMSO-d₆, 500 MHz] δ 7.88 (d, J = 7.5 Hz, 1H), 7.56 (d, J = 7.5 Hz, 1H), 3.99 (q, J = 6.5 Hz, 2H), 3.78-3.40 (m, 2H), 3.20 (q, J = 6.5 Hz, 2H), 2.39-2.10 (m, 4H), 1.36-1.15 (m, 6H). |
| 103 | pyrrolidinone | Et | Et | 1-methyl-3-methyl-pyrazole-4-carbonyl | [DMSO-d₆, 500 MHz] δ 8.17 (s, 1H), 7.86 (d, J = 7.5 Hz, 1H), 7.56 (d, J = 7.5 Hz, 1H), 4.02-3.90 (m, 5H), 3.81-3.41 (m, 2H), 3.21 (q, J = 6.5 Hz, 2H), 2.50 (s, 3H), 2.39-2.05 (m, 4H), 1.36-1.18 (m, 6H). |
| 104 | pyrrolidinone | cyclopropyl | Et | H | [DMSO-d₆, 500 MHz] δ 7.83 (d, J = 7.5 Hz, 1H), 7.61 (d, J = 7.5 Hz, 1H), 3.99 (q, J = 6.5 Hz, 2H), 3.70-3.54 (m, 2H), 2.60- 2.44 (m, 3H), 2.35-2.20 (m, 2H), 1.44-0.59 (m, 7H). |
| 105 | pyrrolidinone | cyclopropyl | Et | 1-methyl-3-methyl-pyrazole-4-carbonyl | [DMSO-d₆, 500 MHz] δ 8.15 (s, 1H), 7.83 (d, J = 7.5 Hz, 1H), 7.61 (d, J = 7.5 Hz, 1H), 4.00 (q, J = 6.5 Hz, 2H), 3.80 (s, 3H), 3.70-3.54 (m, 2H), 2.60-2.50 (m, 2H), 2.44 (s, 3H), 2.35-2.20 (m, 3H), 1.41-0.61 (m, 7H). |
| 106 | piperidinone | H | Et | H | [DMSO-d₆, 500 MHz] δ 7.85 (d, J = 7.5 Hz, 1H), 7.69 (s, 1H), 7.55 (d, J = 7.5 Hz, 1H), 4.01 (q, J = 6.5 Hz, 2H), 3.39-3.32 (m, 2H), 2.25-2.07 (m, 2H), 1.68-1.31 (m, 7H). |
| 107 | piperidinone | H | Et | 1-methyl-pyrazole-4-carbonyl | [DMSO-d₆, 500 MHz] δ 8.11 (s, 1H), 7.85 (d, J = 7.5 Hz, 1H), 7.70 (s, 1H), 7.54 (d, J = 7.5 Hz, 1H), 3.99 (q, J = 6.5 Hz, 2H), 3.76 (s, 3H), 3.42-3.31 (m, 2H), 2.46-2.40 (m, 5H), 1.68-1.30 (m, 7H). |

-continued

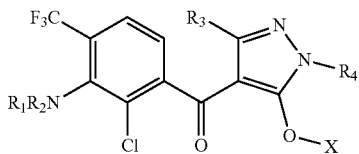

I

| compound ID | R₁R₂N = | R₃ = | R₄ = | X = | HNMR |
|---|---|---|---|---|---|
| 108 | piperidin-2-one-N-yl | Me | Et | H | [DMSO-d$_6$, 500 MHz] δ 7.65 (d, J = 7.5 Hz, 1H), 7.46 (s, 1H), 4.02 (q, J = 6.5 Hz, 2H), 3.39-3.31 (m, 2H), 2.46-2.41 (m, 5H), 1.68-1.32 (m, 7H). |
| 109 | piperidin-2-one-N-yl | Me | Et | 1,3-dimethyl-1H-pyrazol-4-yl carbonyl | [DMSO-d$_6$, 500 MHz] δ 8.15 (s, 1H), 7.68 (d, J = 7.5 Hz, 1H), 7.47 (s, 1H), 4.05 (q, J = 6.5 Hz, 2H), 3.76 (s, 3H), 3.41-3.30 (m, 5H), 2.46-2.43 (m, 5H), 1.68-1.30 (m, 7H). |
| 110 | piperidin-2-one-N-yl | Et | Me | H | [DMSO-d$_6$, 500 MHz] δ 7.68 (d, J = 7.5 Hz, 1H), 7.49 (s, 1H), 3.41-3.30 (m, 7H), 2.45-2.33 (m, 2H), 1.68-1.30 (m, 7H). |
| 111 | piperidin-2-one-N-yl | Et | Me | 1,3-dimethyl-1H-pyrazol-4-yl carbonyl | [DMSO-d$_6$, 500 MHz] δ 8.19 (s, 1H), 7.66 (d, J = 7.5 Hz, 1H), 7.45 (s, 1H), 4.02 (s, 3H), 3.40-3.28 (m, 7H), 2.48-2.38 (m, 5H), 1.68-1,28 (m, 7H). |
| 112 | piperidin-2-one-N-yl | Et | Et | H | [DMSO-d$_6$, 500 MHz] δ 7.71 (d, J = 7.5 Hz, 1H), 7.50 (s, 1H), 4.15-4.02 (m, 4H), 3.39-3.21 (m, 2H), 2.46-2.25 (m, 4H), 1.68-1.30 (m, 8H). |
| 113 | piperidin-2-one-N-yl | Et | Et | 1,3-dimethyl-1H-pyrazol-4-yl carbonyl | [DMSO-d$_6$, 500 MHz] δ 8.19 (s, 1H), 7.71 (d, J = 7.5 Hz, 1H), 7.50 (s, 1H), 4.15-4.02 (m, 7H), 3.39-3.28 (m, 2H), 2.46-2.28 (m, 7H), 1.68-1.30 (m, 8H). |
| 114 | piperidin-2-one-N-yl | cyclopropyl | Et | H | [DMSO-d$_6$, 500 MHz] δ 7.68 (d, J = 7.5 Hz, 1H), 7.46 (s, 1H), 4.00 (q, J = 6.5 Hz, 2H), 3.39-3,31 (m, 2H), 2.92-2.86 (m, 1H), 2.46-2.31 (m, 2H), 1.68-0.61 (m, 11H). |

-continued

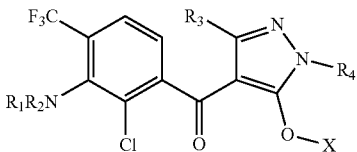

I

| compound ID | R₁R₂N = | R₃ = | R₄ = | X = | HNMR |
|---|---|---|---|---|---|
| 115 | piperidin-2-one (N-linked) | cyclopropyl | Et | -C(O)-(1,3-dimethylpyrazol-4-yl), Me at 3 | [DMSO-d₆, 500 MHz] δ 8.15 (s, 1H), 7.68 (d, J = 7.5 Hz, 1H), 7.46 (s, 1H), 4.12-3.95 (m, 5H), 3.39-3.31 (m, 2H), 2.92-2.81 (m, 1H), 2.52-2.43 (m, 5H), 1.68-0.61 (m, 11H). |
| 116 | azepan-2-one (N-linked) | H | Et | H | [DMSO-d₆, 500 MHz] δ 7.85 (d, J = 7.5 Hz, 1H), 7.69 (s, 1H), 7.55 (d, J = 7.5 Hz, 1H), 4.02 (q, J = 6.5 Hz, 2H), 3.60-3.50 (m, 2H), 2.25-2.01 (m, 4H), 1.68-1.40 (m, 4H), 1.35 (t, J = 6.5 Hz, 3H). |
| 117 | azepan-2-one (N-linked) | H | Et | -C(O)-(1,3-dimethylpyrazol-4-yl) | [DMSO-d₆, 500 MHz] δ 8.15 (s, 1H), 7.85 (d, J = 7.5 Hz, 1H), 7.70 (s, 1H), 7.55 (d, J = 7.5 Hz, 1H), 4.10-4.01 (m, 5H), 3.60-3.51 (m, 2H), 2.53 (s, 3H), 2.26-2.01 (m, 4H), 1.68-1.40 (m, 4H), 1.35 (t, J = 6.5 Hz, 3H). |
| 118 | azepan-2-one (N-linked) | Me | Et | H | [DMSO-d₆, 500 MHz] δ 7.85 (d, J = 7.5 Hz, 1H), 7.55 (d, J = 7.5 Hz, 1H), 4.00 (q, J = 6.5 Hz, 2H), 3.60-3.50 (m, 2H), 2.36 (s, 3H), 2.25-2.01 (m, 4H), 1.68-1.24 (m, 7H). |
| 119 | azepan-2-one (N-linked) | Me | Et | -C(O)-(1,3-dimethylpyrazol-4-yl) | [DMSO-d₆, 500 MHz] δ 8.14 (s, 1H), 7.85 (d, J = 7.5 Hz, 1H), 7.55 (d, J = 7.5 Hz, 1H), 4.08-3.96 (m, 5H), 3.60-3.51 (m, 2H), 2.52 (s, 3H), 2.38 (s, 3H), 2.28-2.03 (m, 4H), 1.69-1.26 (m, 7H). |
| 120 | azepan-2-one (N-linked) | Et | Me | H | [DMSO-d₆, 500 MHz] δ 7.85 (d, J = 7.5 Hz, 1H), 7.55 (d, J = 7.5 Hz, 1H), 3.60-3.55 (m, 5H), 2.69 (q, J = 6.5 Hz, 2H), 2.25-2.01 (m, 2H), 1.68-1.24 (m, 9H). |
| 121 | azepan-2-one (N-linked) | Et | Me | -C(O)-(1,3-dimethylpyrazol-4-yl) | [DMSO-d₆, 500 MHz] δ 8.21 (s, 1H), 7.85 (d, J = 7.5 Hz, 1H), 7.55 (d, J = 7.5 Hz, 1H), 4.02 (s, 3H), 3.60-3.55 (m, 5H), 2.69 (q, J = 6.5 Hz, 2H), 2.51 (s, 3H), 2.25-2.01 (m, 2H), 1.68-1.24 (m, 9H). |

-continued

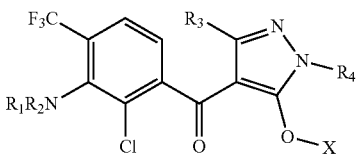

| compound ID | R₁R₂N = | R₃ = | R₄ = | X = | HNMR |
|---|---|---|---|---|---|
| 122 | azepan-2-one (N-linked) | Et | Et | H | [DMSO-d₆, 500 MHz] δ 7.85 (d, J = 7.5 Hz, 1H), 7.55 (d, J = 7.5 Hz, 1H), 4.01 (q, J = 6.5 Hz, 2H), 3.60-3.55 (m, 2H), 2.69 (q, J = 6.5 Hz, 2H), 2.27-2.01 (m, 2H), 1.69-1.25 (m, 12H). |
| 123 | azepan-2-one (N-linked) | Et | Et | 1,3-dimethyl-1H-pyrazol-4-yl carbonyl | [DMSO-d₆, 500 MHz] δ 8.21 (s, 1H), 7.86 (d, J = 7.5 Hz, 1H), 7.55 (d, J = 7.5 Hz, 1H), 4.06-3.95 (m, 5H), 3.60-3.52 (m, 2H), 2.69 (q, J = 6.5 Hz, 2H), 2.45 (s, 3H), 2.25-2.01 (m, 2H), 1.68-1.24 (m, 12H). |
| 124 | azepan-2-one (N-linked) | cyclopropyl | Et | H | [DMSO-d₆, 500 MHz] δ 7.76 (d, J = 7.5 Hz, 1H), 7.58 (d, J = 7.5 Hz, 1H), 3.99 (q, J = 6.5 Hz, 2H), 3.60-3.55 (m, 2H), 2.90-2.75 (m, 1H), 2.25-2.01 (m, 2H), 1.68-1.40 (m, 4H), 1.37-0.61 (m, 9H). |
| 125 | azepan-2-one (N-linked) | cyclopropyl | Et | 1,3-dimethyl-1H-pyrazol-4-yl carbonyl | [DMSO-d₆, 500 MHz] δ 8.13 (s, 1H), 7.76 (d, J = 7.5 Hz, 1H), 7.58 (d, J = 7.5 Hz, 1H), 3.99 (q, J = 6.5 Hz, 2H), 3.81 (s, 3H), 3.60-3.52 (m, 2H), 2.90-2.75 (m, 1H), 2.44 (s, 3H), 2.25-2.01 (m, 2H), 1.68-1.40 (m, 4H), 1.38-0.61 (m, 9H). |
| 126 | 1H-pyrazol-1-yl | H | Et | H | [DMSO-d₆, 500 MHz] δ 7.96-7.71 (m, 5H), 6.57 (s, 1H), 3.97 (q, J = 6.5 Hz, 2H), 1.35 (t, J = 6.5 Hz, 3H). |
| 127 | 1H-pyrazol-1-yl | H | Et | 1,3-dimethyl-1H-pyrazol-4-yl carbonyl | [DMSO-d₆, 500 MHz] δ 8.15 (s, 1H), 7.96-7.71 (m, 5H), 6.57 (s, 1H), 4.01 (q, J = 6.5 Hz, 2H), 3.81 (s, 3H), 2.46 (s, 3H), 1.33 (t, J = 6.5 Hz, 3H). |
| 128 | 1H-pyrazol-1-yl | Me | Et | H | [DMSO-d₆, 500 MHz] δ 7.96-7.71 (m, 4H), 6.56 (m, 1H), 4.00 (q, J = 6.5 Hz, 2H), 2.46 (s, 3H), 1.33 (t, J = 6.5 Hz, 3H). |
| 129 | 1H-pyrazol-1-yl | Me | Et | 1,3-dimethyl-1H-pyrazol-4-yl carbonyl | [DMSO-d₆, 500 MHz] δ 8.15 (s, 1H), 7.96-7.71 (m, 4H), 6.56 (s, 1H), 3.99 (q, J = 6.5 Hz, 2H), 3.81 (s, 3H), 2.46 (s, 3H), 2.40 (s, 3H), 1.32 (t, J = 6.5 Hz, 3H). |

-continued

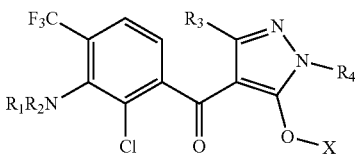

| compound ID | R₁R₂N = | R₃ = | R₄ = | X = | HNMR |
|---|---|---|---|---|---|
| 130 | pyrazol-1-yl | Et | Me | H | [DMSO-d₆, 500 MHz] δ 8.02-7.76 (m, 4H), 6.61 (m, 1H), 3.58 (s, 3H), 3.15 (q, J = 6.5 Hz, 2H), 1.34 (t, J = 6.5 Hz, 3H). |
| 131 | pyrazol-1-yl | Et | Me | -C(O)-(1,3-dimethylpyrazol-4-yl) | [DMSO-d₆, 500 MHz] δ 8.21 (s, 1H), 8.02-7.76 (m, 4H), 6.61 (m, 1H), 4.05 (s, 3H), 3.58 (s, 3H), 3.15 (q, J = 6.5 Hz, 2H), 2.55 (s, 3H), 1.34 (t, J = 6.5 Hz, 3H). |
| 132 | pyrazol-1-yl | Et | Et | H | [DMSO-d₆, 500 MHz] δ 8.02-7.76 (m, 4H), 6.61 (m, 1H), 3.96 (q, J = 6.5 Hz, 2H), 3.15 (q, J = 6.5 Hz, 2H), 1.36-1.30 (m, 6H). |
| 133 | pyrazol-1-yl | Et | Et | -C(O)-(1,3-dimethylpyrazol-4-yl) | [DMSO-d₆, 500 MHz] δ 8.25 (s, 1H), 8.02-7.70 (m, 4H), 6.61 (m, 1H), 4.05-3.90 (m, 5H), 3.17 (q, J = 6.5 Hz, 2H), 2.55 (s, 3H), 1.38-1.30 (m, 6H). |
| 134 | pyrazol-1-yl | cyclopropyl | Et | H | [DMSO-d₆, 500 MHz] δ 7.92-7.63 (m, 4H), 6.58 (m, 1H), 3.98 (q, J = 6.5 Hz, 2H), 2.72-2.58 (m, 1H), 1.42-0.65 (m, 7H). |
| 135 | pyrazol-1-yl | cyclopropyl | Et | -C(O)-(1,3-dimethylpyrazol-4-yl) | [DMSO-d₆, 500 MHz] δ 8.15 (s, 1H), 7.92-7.63 (m, 4H), 6.58 (m, 1H), 4.00 (q, J = 6.5 Hz, 2H), 3.81 (s, 3H), 2.72-2.58 (m, 1H), 2.40 (s, 3H), 1.42-0.65 (m, 7H). |
| 136 | 4-methylpyrazol-1-yl | H | Et | H | [DMSO-d₆, 500 MHz] δ 8.03 (s, 1H), 7.95-7.55 (m, 4H), 4.00 (q, J = 6.5 Hz, 2H), 2.11 (s, 3H), 1.35 (t, J = 6.5 Hz, 3H). |
| 137 | 4-methylpyrazol-1-yl | H | Et | -C(O)-(1,3-dimethylpyrazol-4-yl) | [DMSO-d₆, 500 MHz] δ 8.15 (s, 1H), 8.03 (s, 1H), 7.95-7.50 (m, 4H), 3.99 (q, J = 6.5 Hz, 2H), 3.80 (s, 3H), 2.44 (s, 3H), 2.12 (s, 3H), 1.33 (t, J = 6.5 Hz, 3H). |
| 138 | 4-methylpyrazol-1-yl | Me | Et | H | [DMSO-d₆, 500 MHz] δ 7.85-7.80 (m, 2H), 7.69-7.60 (m, 2H), 3.99 (q, J = 6.5 Hz, 2H), 2.23 (s, 3H), 2.12 (s, 3H), 1.36 (t, J = 6.5 Hz, 3H). |

-continued

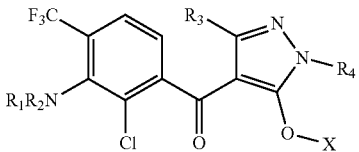

I

| compound ID | R₁R₂N = | R₃ = | R₄ = | X = | HNMR |
|---|---|---|---|---|---|
| 139 | 4-Me-pyrazol-1-yl | Me | Et | -C(O)-(1,3-diMe-pyrazol-4-yl) | [DMSO-d₆, 500 MHz] δ 8.15 (s, 1H), 7.85-7.80 (m, 2H), 7.69-7.60 (m, 2H), 3.98 (q, J = 6.5 Hz, 2H), 2.44 (s, 3H), 2.20 (s, 3H), 2.10 (s, 3H), 1.32 (t, J = 6.5 Hz, 3H). |
| 140 | 4-Me-pyrazol-1-yl | Et | Me | H | [DMSO-d₆, 500 MHz] δ 7.88-7.81 (m, 2H), 7.71-7.61 (m, 2H), 3.68 (s, 3H), 3.18 (q, J = 6.5 Hz, 2H), 2.12 (s, 3H), 1.36 (t, J = 6.5 Hz, 3H). |
| 141 | 4-Me-pyrazol-1-yl | Et | Me | -C(O)-(1,3-diMe-pyrazol-4-yl) | [DMSO-d6, 500 MHz] δ 8.21 (s, 1H), 7.88-7.81 (m, 2H), 7.71-7.61 (m, 2H), 4.02 (s, 3H), 3.68 (s, 3H), 3.18 (q, J = 6.5 Hz, 2H), 2.55 (s, 3H), 2.12 (s, 3H), 1.36 (t, J = 6.5 Hz, 3H). |
| 142 | 4-Me-pyrazol-1-yl | Et | Et | H | [DMSO-d₆, 500 MHz] δ 7.88-7.81 (m, 2H), 7.71-7.61 (m, 2H), 4.00 (q, J = 6.5 Hz, 2H), 3.18 (q, J = 6.5 Hz, 2H), 2.12 (s, 3H), 1.36 (m, 6H). |
| 143 | 4-Me-pyrazol-1-yl | Et | Et | -C(O)-(1,3-diMe-pyrazol-4-yl) | [DMSO-d₆, 500 MHz] δ 8.22 (s, 1H), 7.88-7.81 (m, 2H), 7.71-7.61 (m, 2H), 4.05-3.96 (m, 5H), 3.18 (q, J = 6.5 Hz, 2H), 2.55 (s, 3H), 2.12 (s, 3H), 1.36 (m, 6H). |
| 144 | 4-Me-pyrazol-1-yl | cyclopropyl | Et | H | [DMSO-d₆, 500 MHz] δ 7.81-7.63 (m, 3H), 7.58 (s, 1H), 4.05 (q, J = 6.5 Hz, 2H), 2.92-2.58 (m, 1H), 2.13 (s, 3H), 1.42-0.65 (m, 7H). |
| 145 | 4-Me-pyrazol-1-yl | cyclopropyl | Et | -C(O)-(1,3-diMe-pyrazol-4-yl) | [DMSO-d₆, 500 MHz] δ 8.13 (s, 1H), 7.81-7.63 (m, 3H), 7.58 (s, 1H), 4.05 (q, J = 6.5 Hz, 2H), 3.81 (s, 3H), 2.92-2.58 (m, 1H), 2.44 (s, 3H), 2.13 (s, 3H), 1.42-0.65 (m, 7H). |
| 146 | 2-oxopiperidin-1-yl | cyclopropyl | n-Bu | H | [DMSO-d₆, 500 MHz] δ 7.70 (d, J = 7.5 Hz, 1H), 7.47 (d, J = 7.5 Hz, 1H), 4.02-3.83 (m, 5H), 2.95-2.88 (m, 1H), 2.50-2.38 (m, 2H), 1.70-0.65 (m, 12H). |

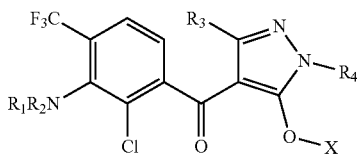

| compound ID | $R_1R_2N =$ | $R_3 =$ | $R_4 =$ | $X =$ | HNMR |
|---|---|---|---|---|---|
| 147 | piperidin-2-one-N-yl | cyclopropyl | isopropyl (Me, Me) | H | [DMSO-$d_6$, 500 MHz] δ 7.74 (d, J = 7.5 Hz, 1H), 7.50 (d, J = 7.5 Hz, 1H), 4.05-3.85 (m, 3H), 3.00-2.89 (m, 1H), 2.50-2.38 (m, 2H), 1.68-0.65 (m, 14H). |
| 148 | piperidin-2-one-N-yl | cyclopropyl | cyclopropyl | H | [DMSO-$d_6$, 500 MHz] δ 7.70 (d, J = 7.5 Hz, 1H), 7.48 (s, 1H), 4.01-.86 (m, 2H), 2.52-2.01 (m, 6H), 1.69-0.50 (m, 10H). |

Embodiments of the representative compounds are as follows:

1. The Preparation of Compound 002

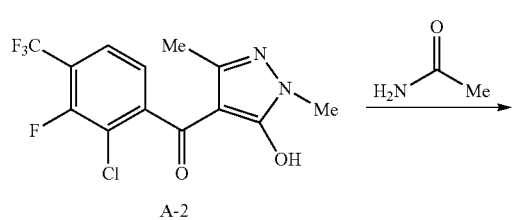

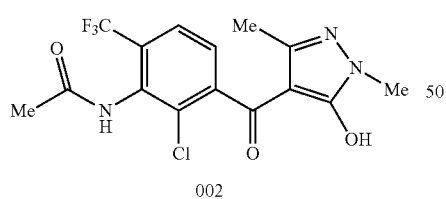

7 g of acetamide was dissolved in 100 ml of DMF and cooled to 0° C. 5 g of 60% NaH was added and stirred for 1 hour followed by an addition of 15 g of intermediate (A-2). The reaction solution was heated to 55° C. and stirred until the raw materials were completely consumed. Then cooled to RT. DMF was removed under reduced pressure. Diluted hydrochloric acid was added to the residue to adjust pH to 2~3 and precipitate solid. The solid was collected by sucking filtration. The filter cake was dried to obtain 14 g of off-white solid (002) with yield of 82.8% and HPLC purity of 99.03%.

2. The Preparation of Compound 001

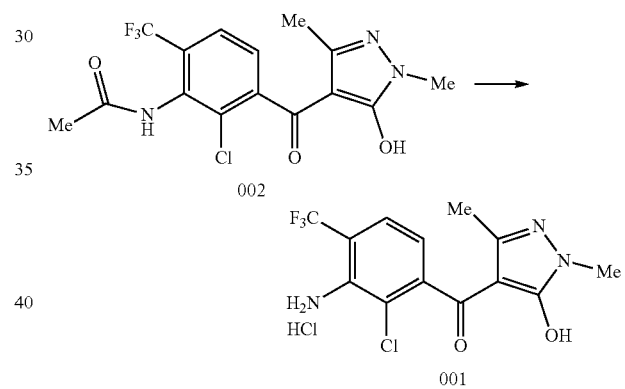

3 g of intermediate (002), 40 ml of concentrated hydrochloric acid and 30 ml of water were mixed with 10 ml of 95% ethanol, then stirred at reflux for 4 hours. The solvent was removed by evaporation to obtain 2.9 g of faint yellow solid (001) with 98.0% yield and 91.41% HPLC purity.

3. The Preparation of Compound 004

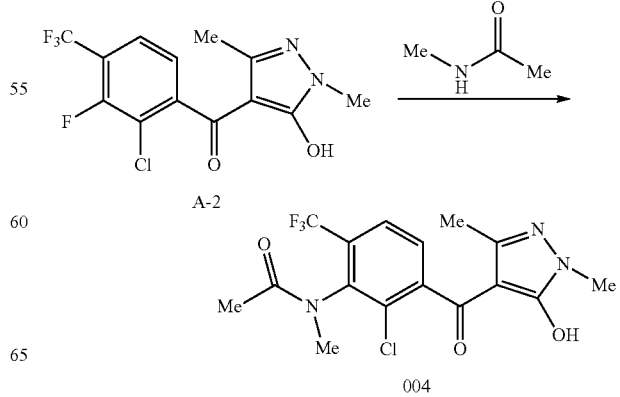

0.8 g of N-methyl acetamide was dissolved into 10 ml of DMF and cooled to 0° C. 0.5 g of 60% NaH was added, and the reaction solution was stirred for 1 hour. Then 1.5 g of intermediate (A-2) was added. The reaction solution was heated to 55° C. and stirred until the raw materials were completely consumed. Then cooled to RT and DMF was remove under reduced pressure. Diluted hydrochloric acid was added to the residue to adjust pH to 2~3 and precipitate solid. The solid was collected by sucking filtration. The filter cake was dried to obtain 1.1 g of faint yellow solid (004) with yield of 62.7% and HPLC purity of 72.19%.

4. The Preparation of Compound 018

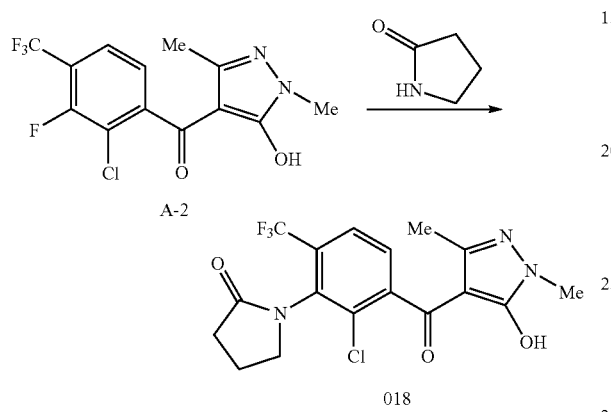

0.5 g of 60% NaH was added to 10 ml of DMF and cooled to 0° C. 1.1 g of 2-pyrrolidone was added. The reaction solution was stirred for 1 hour followed by an addition of 1.5 g of intermediate (A-2). The reaction solution was heated to 55-60° C. and reacted for 3 hours, then cooled to RT. Diluted hydrochloric acid was added to the reaction solution to adjust pH to 2~3. The solution was extracted with ethyl acetate. The organic phase was washed with water and saturated sodium chloride solution, dried and concentrated to obtain 1.3 g of faint yellow solid (018) with yield of 71.9% and HPLC purity of 96.02%.

5. The Preparation of Compound 021.

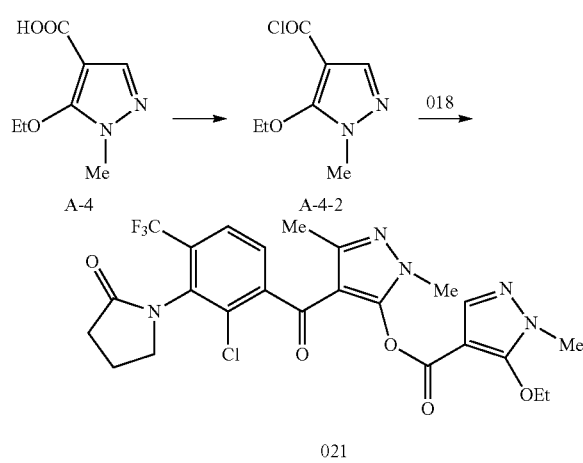

5 g of intermediate (A-4) was mixed with 15 ml of sulfoxide chloride and stirred at reflux for 1 hour. The excessive sulfoxide chloride was removed under reduced pressure to obtain 5 g of faint yellow liquid (A-4-2). The yield is 90.4%. The crude product was used directly for further reaction without purification.

2 g of intermediate (018) was dissolved in 10 ml of DMF, and 1.4 g of anhydrous potassium carbonate was added, then stirred at RT for 2 hours. 2 ml of DMF solution dissolved with 1 g of intermediate (A-4-2) was added dropwise and stirred overnight at RT after the addition. To the reaction solution was added with water and extracted with ethyl acetate. The organic phase was washed with water, 5% hydrochloric acid, 5% potassium carbonate solution, water and saturated sodium chloride solution successively, dried and concentrated to obtain 2.2 g of yellow solid (021) with yield of 79.6% and HPLC purity of 85.38%.

6. The Preparation of Compound 021

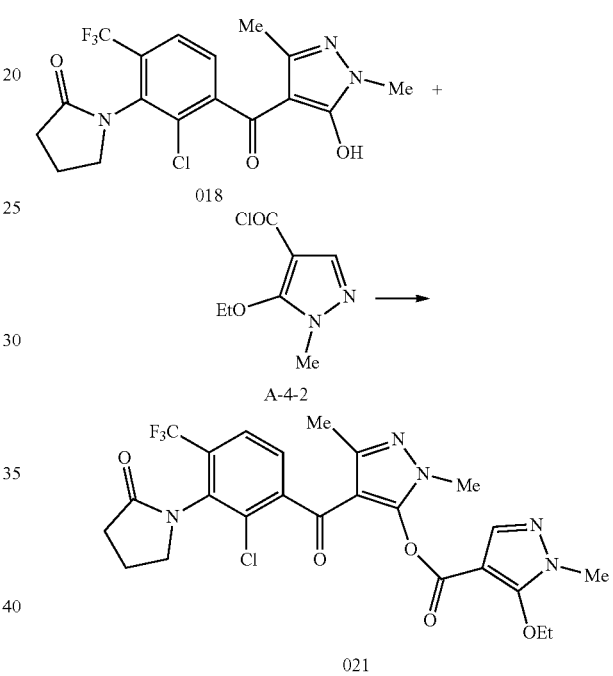

2 g of intermediate (018) was dissolved in 10 ml of acetonitrile and 1.5 g of triethylamine was added. Then cooled to 0° C. and 2 ml of acetonitrile solution dissolved with 1 g of intermediate (A-4-2) was added dropwise, and stirred overnight at RT after the addition. Water was added to the reaction solution and extracted with ethyl acetate. The organic phase was washed with water, 5% hydrochloric acid, 5% potassium carbonate solution, water and saturated sodium chloride solution successively, dried and concentrated to obtain 2.1 g of yellow solid (021) with yield of 75.8% and HPLC purity of 83.10%.

7. The Preparation of Compound 021.

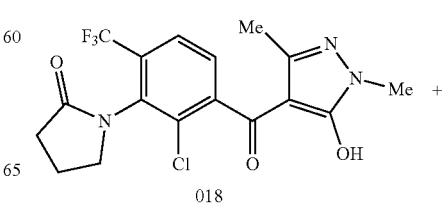

-continued

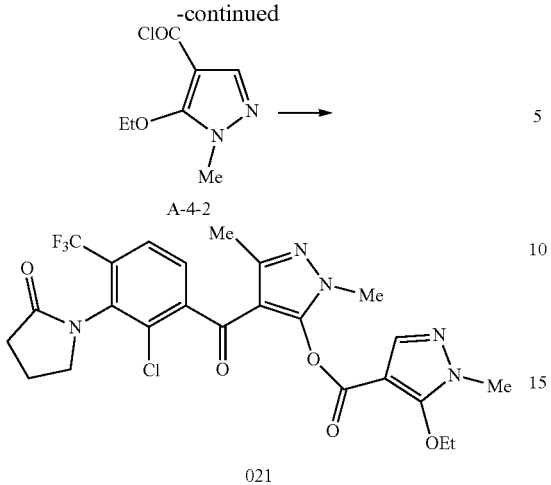

2 g of intermediate (018) was dissolved in 10 ml of acetonitrile, then cooled to 0° C. followed by an addition of 0.5 g of 60% NaH. 2 ml of acetonitrile solution with 1 g of intermediate (A-4-2) was added dropwise after being stirred for 1 hour. The reaction solution was then stirred overnight at RT. The reaction solution was added with water and extracted with ethyl acetate. The organic phase was washed with water, 5% hydrochloric acid, 5% potassium carbonate solution, water and saturated sodium chloride solution successively, dried and concentrated to obtain 2.1 g of yellow solid (021) with yield of 75.8% and HPLC purity of 80.15%.

8. The Preparation of Compound 068.

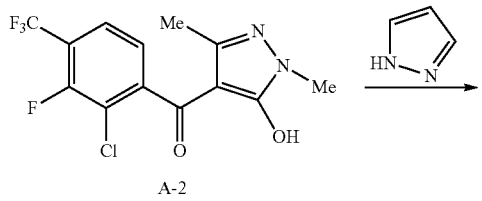

0.8 g of pyrazole was dissolved in 10 ml of acetonitrile. Then cooled to 0° C. followed by an addition of 0.5 g of 60% NaH, and stirred for 1 hour. The reaction solution was added with 1.5 g of intermediate (A-2) and then stirred overnight at RT. Hydrochloric acid was added to the reaction solution to adjust pH to 2~3 and precipitate solid. The solid was collected by sucking filtration, then dried to give 1.8 g of white solid (068) with yield of 99% and HPLC purity of 96.90%.

9. The Preparation of Compound 070.

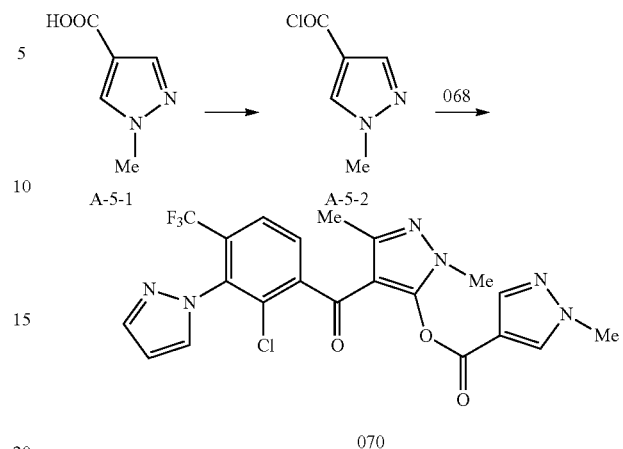

5 g of 1-methylpyrazole-4-formic acid was mixed with 10 ml of sulfoxide chloride. The mixture was stirred at reflux for 1 hour. Excessive sulfoxide chloride was removed by reduced pressure distillation to obtain 5 g of dark brown solid (A-5-2). The yield is 86.0%. The product was used directly for the next step reaction without purification.

1.9 g of intermediate (068) was dissolved in 10 ml of DMF followed by an addition of 1.4 g of anhydrous potassium carbonate. The mixture was stirred at RT for 2 hours, then 2 ml of DMF solution with 0.8 g of (A-5-2) was added, and then stirred overnight at RT. The reaction solution was added with water and extracted with ethyl acetate. The organic phase was washed with water, 5% hydrochloric acid, 5% potassium carbonate solution, water and saturated sodium chloride solution successively, dried and concentrated to obtain 2.0 g of yellow solid (070) with yield of 81.1% and HPLC purity of 74.87%.

10. The Preparation of Compound 095.

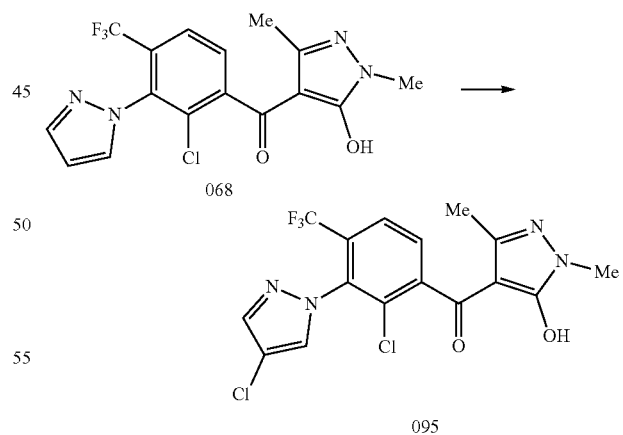

1.2 g of intermediate (068) was dissolved in 12 ml of water. 5 ml of sodium hypochlorite solution was added dropwise slowly with stirring. Then stirred for 1 hour at RT. Diluted hydrochloric acid was added to adjust pH to 2~3, and extracted with dichloroethane. The organic phase was washed with water and saturated sodium chloride solution, dried and concentrated to obtain 0.4 g of yellow solid (095) with yield of 30.7% and HPLC purity of 82.63%.

Biological Activity Evaluation:

The activity level standard of harmful plant destruction (i.e. growth control rate) is as follows:
Level 10: completely dead;
Level 9: above 95% growth control rate;
Level 8: above 90% growth control rate;
Level 7: above 80% growth control rate;
Level 6: above 70% growth control rate;
Level 5: above 60% growth control rate;
Level 4: above 50% growth control rate;
Level 3: above 20% growth control rate;
Level 2: 5%-20% growth control rate;
Level 1: below 5% growth control rate;

The above described growth control rate is fresh weight control rate.

Monocotyledonous and dicotyledonous weed seeds and main crop seeds (i.e. wheat, corn, rice, soybean, cotton, oilseed, millet and *sorghum*.) were put into a plastic pot loaded with soil. Then covered with 0.5-2 cm soil, the seeds were allowed to grow in good greenhouse environment. The test plants were treated at 4-5 leaf stage 2-3 weeks after sowing. The test compounds of the invention were dissolved with acetone respectively, then added with 80 tween and diluted by certain amount of water to certain concentration. The solution was sprayed to the plants with a sprayer. Then the plants were cultured for 3 weeks in the greenhouse. The experiment result of weed controlling effect after 3 weeks was listed in table 1.

TABLE 1 experiment on weed control effect in post-emergence stage

| Compound ID | *Echinochloa* | Crab grass | Green foxtail | *Rorippa indica* | Indian mallow | *Bidens bipinnata* | Corn | Wheat | Rice |
|---|---|---|---|---|---|---|---|---|---|
| 1 | 6 | 1 | 6 | 9 | 9 | 8 |  | 0 | 4 |
| 2 | 8 | 4 | 7 | 9 | 10 | 8 |  | 5 | 7 |
| 4 | 4 | 4 | 1 | 9 | 9 | 9 |  | 0 | 5 |
| 5 | 10 | 2 | 5 | 10 | 10 | 10 |  | 0 | 7 |
| 6 | 10 | 2 | 3 | 5 | 0 | 5 |  | 0 | 1 |
| 8 | 10 | 3 | 10 | 0 | 3 | 10 |  | 0 | 0 |
| 9 | 10 | 1 | 9 | 0 | 2 | 5 |  | 0 | 5 |
| 10 | 6 | 1 | 5 | 0 | 0 | 5 |  | 0 | 0 |
| 11 | 1 | 1 | 1 | 0 | 0 | 5 |  | 0 | 0 |
| 12 | 9 | 1 | 2 | 0 | 10 | 10 |  | 0 | 0 |
| 14 | 5 | 10 | 10 | 10 | 7 | 8 | 8 | 3 | 3 |
| 15 | 5 | 9 | 10 | 9 | 8 | 8 | 9 | 2 | 2 |
| 16 | 10 | 10 | 10 | 10 | 10 | 5 | 3 | 3 | 4 |
| 17 | 6 | 10 | 10 |  | 10 | 5 | 4 | 1 | 7 |
| 18 | 8 | 10 | 10 | 10 | 9 | 10 |  | 3 |  |
| 19 | 9 | 9 | 10 | 9 | 10 | 9 |  | 0 | 7 |
| 20 | 10 | 10 | 10 | 9 | 10 | 9 |  | 0 | 8 |
| 21 | 6 | 7 | 10 |  | 9 |  | 3 | 3 | 5 |
| 23 | 10 | 10 | 10 | 10 | 10 | 10 | 5 | 4 | 4 |
| 25 | 6 | 6 | 10 | 10 | 10 | 8 | 4 | 3 | 6 |
| 26 | 6 | 10 | 10 |  | 10 | 5 | 4 | 4 | 8 |
| 27 | 7 | 8 | 10 | 7 | 10 | 8 | 4 | 3 | 7 |
| 28 | 5 | 4 | 1 | 10 | 10 | 7 | 1 | 0 | 1 |
| 29 | 5 | 7 | 9 | 7 | 7 | 7 | 7 | 3 | 1 |
| 30 | 5 | 8 | 9 | 10 | 6 | 5 | 9 | 4 | 1 |
| 31 | 5 | 9 | 10 | 8 | 7 | 6 | 9 | 3 | 1 |
| 32 | 9 | 10 | 10 | 10 | 10 | 6 | 4 | 1 | 8 |
| 33 | 9 | 9 | 10 | 10 | 10 | 9 | 3 | 2 | 8 |
| 34 | 10 | 10 | 5 | 10 | 9 | 4 | 3 | 1 | 3 |
| 35 | 7 | 8 | 10 | 9 | 9 | 9 |  | 0 | 6 |
| 36 | 7 | 5 | 10 | 5 | 5 | 6 | 0 | 3 | 8 |
| 37 | 10 | 6 | 10 | 10 | 10 | 10 | 0 | 0 | 3 |
| 38 | 9 | 6 | 10 | 10 | 10 | 2 | 0 | 1 | 6 |
| 39 | 10 | 9 | 10 | 10 | 10 | 2 | 2 |  | 6 |
| 46 | 6 | 6 | 10 | 10 | 10 | 2 | 4 | 0 | 5 |
| 48 | 6 | 7 | 8 | 10 | 10 | 4 | 3 | 1 | 5 |
| 49 | 6 | 6 | 9 | 10 | 10 | 4 | 2 | 3 | 7 |
| 50 | 2 | 3 | 7 | 5 | 9 | 3 | 3 | 0 | 0 |
| 51 | 6 | 5 | 0 | 10 | 10 | 2 | 2 | 0 | 1 |
| 52 | 5 | 4 | 1 | 10 | 10 | 1 | 1 | 0 | 1 |
| 54 | 6 | 1 | 5 | 9 | 9 | 9 |  | 0 | 4 |
| 55 | 8 | 4 | 9 | 2 | 10 | 10 | 0 | 0 | 6 |
| 56 | 5 | 3 | 1 | 10 | 10 | 5 | 0 | 0 | 3 |
| 57 | 4 | 1 | 1 | 10 | 10 | 5 | 0 | 0 | 3 |
| 58 | 4 | 1 | 1 | 10 | 10 | 4 | 1 | 0 | 2 |
| 59 | 6 | 5 | 9 | 10 | 10 |  | 1 | 2 | 3 |
| 60 | 5 | 3 | 1 | 10 | 10 | 7 | 0 | 0 | 1 |
| 61 | 5 | 4 | 1 | 10 | 10 | 7 | 1 | 0 | 1 |
| 62 | 7 | 8 | 3 | 10 | 10 |  | 1 | 3 | 5 |
| 63 | 1 | 0 | 1 | 9 | 10 | 10 |  | 0 |  |
| 64 | 5 | 7 | 10 | 9 | 10 | 7 | 7 | 3 | 2 |
| 65 | 7 | 8 | 10 | 9 | 9 | 7 | 9 | 3 | 3 |
| 66 | 6 | 6 | 10 |  | 10 | 6 | 3 | 0 | 3 |
| 67 | 7 | 7 | 10 | 10 | 10 |  | 3 | 0 | 3 |
| 68 | 10 | 5 | 10 | 9 | 10 | 10 |  | 3 | 5 |
| 69 | 6 | 3 | 10 | 0 | 10 | 10 | 0 | 0 | 5 |

TABLE 1-continued

| | experiment on weed control effect in post-emergence stage | | | | | | | |
|---|---|---|---|---|---|---|---|---|
| Compound ID | *Echinochloa* | Crab grass | Green foxtail | *Rorippa indica* | Indian mallow | *Bidens bipinnata* | Corn | Wheat | Rice |
| 70 | 6 | 4 | 9 | 5 | 10 | 5 | 3 | 0 | 3 |
| 71 | 6 | 4 | 8 | 10 | 10 | 7 | 1 | 0 | 1 |
| 72 | 6 | 4 | 10 | 10 | 10 |  | 3 | 0 | 4 |
| 73 | 5 | 5 | 10 | 7 | 10 | 2 | 3 | 1 | 8 |
| 74 | 6 | 4 | 9 | 10 | 10 | 4 | 3 | 1 | 9 |
| 75 | 6 | 4 | 10 | 10 | 10 |  | 3 | 2 | 7 |
| 76 | 7 | 5 | 10 |  | 10 | 4 | 4 | 2 | 9 |
| 77 | 10 | 4 | 7 | 10 | 10 | 9 |  | 0 | 6 |
| 78 | 7 | 4 | 7 | 0 | 10 | 10 | 0 | 0 | 4 |
| 80 | 5 | 6 | 10 | 7 | 7 | 8 | 3 | 2 | 1 |
| 81 | 10 | 7 | 8 | 10 | 10 | 10 | 2 | 0 | 3 |
| 82 | 10 | 6 | 10 | 10 | 9 | 4 | 3 | 0 | 3 |
| 83 | 6 | 6 | 8 |  | 10 | 5 | 4 | 0 | 2 |
| 84 | 10 | 8 | 10 | 9 | 10 | 10 |  | 0 | 7 |
| 85 | 9 | 8 | 10 | 2 | 10 | 10 | 0 | 0 | 6 |
| 86 | 5 | 4 | 2 | 10 | 10 | 6 | 0 | 0 | 2 |
| 87 | 6 | 9 | 10 |  | 10 | 5 | 4 | 0 | 6 |
| 88 | 10 | 9 | 10 | 10 | 10 | 4 | 0 | 0 |  |
| 89 | 5 | 1 | 2 | 9 | 10 | 3 | 1 | 0 | 1 |
| 90 | 6 | 1 | 2 | 10 | 10 |  | 1 | 0 | 2 |
| 91 | 6 | 2 | 7 |  | 10 | 5 | 1 | 1 | 6 |
| 92 | 6 | 3 | 8 | 10 | 10 | 8 | 2 | 1 | 2 |
| 93 | 5 | 2 | 2 | 0 | 5 | 5 |  | 0 | 0 |
| 94 | 1 | 3 | 1 | 0 | 3 | 2 | 1 | 0 | 0 |
| 95 | 1 | 1 | 1 | 0 | 0 |  |  | 0 | 6 |
| 96 | 10 | 5 | 10 | 10 | 10 | 10 | 0 | 1 | 9 |
| 97 | 10 | 3 | 10 | 10 | 10 | 10 | 1 | 1 | 7 |
| 99 | 10 | 10 | 10 | 10 | 3 | 10 | 4 | 4 | 10 |
| 100 | 10 | 3 | 10 | 10 | 9 | 9 | 2 | 2 | 10 |
| 101 | 10 | 4 | 10 | 10 | 10 | 9 | 2 | 3 | 10 |
| 104 | 10 | 9 | 10 | 10 | 10 | 7 | 4 | 5 | 10 |
| 105 | 10 | 10 | 10 | 10 | 9 | 10 | 5 | 5 | 10 |
| 106 | 10 | 6 | 3 | 5 | 7 | 6 | 3 | 3 | 9 |
| 107 | 10 | 8 | 10 | 6 | 10 | 9 | 5 | 5 | 8 |
| 110 | 9 | 2 | 10 | 10 | 9 | 5 | 0 | 2 | 10 |
| 111 | 10 | 3 | 2 | 10 | 10 | 4 | 1 | 1 | 10 |
| 112 | 10 | 6 | 5 | 2 | 5 | 1 | 3 | 3 | 7 |
| 115 | 9 | 2 | 10 | 10 | 10 | 6 | 3 | 1 | 8 |
| 117 | 10 | 3 | 10 | 5 | 9 | 10 | 0 | 0 | 9 |
| 118 | 9 | 1 | 10 | 5 | 0 | 1 | 2 | 1 | 1 |
| 119 | 10 | 5 | 9 | 10 | 3 | 5 | 3 | 1 | 6 |
| 120 | 10 | 1 | 7 | 10 | 4 | 4 | 1 | 1 | 5 |
| 121 | 10 | 4 | 9 | 10 | 5 | 3 | 1 | 1 | 6 |
| 122 | 9 | 3 | 10 | 0 | 5 | 5 | 0 | 1 | 5 |
| 123 | 10 | 3 | 6 | 3 | 10 | 7 | 4 | 1 | 7 |
| 125 | 8 | 10 | 10 | 4 | 10 | 10 | 5 | 2 | 10 |
| 127 | 10 | 3 | 10 | 10 | 10 | 10 | 1 | 1 | 7 |
| 128 | 10 | 1 | 10 | 7 | 3 | 6 | 0 | 0 | 5 |
| 129 | 10 | 0 | 10 | 10 | 3 | 9 | 3 | 1 | 6 |
| 130 | 10 | 3 | 10 | 10 | 0 | 3 | 4 | 2 | 7 |
| 131 | 10 | 3 | 10 | 10 | 10 | 10 | 4 | 0 | 10 |
| 132 | 9 | 3 | 10 | 0 | 5 | 5 | 0 | 1 | 5 |
| 133 | 10 | 2 | 8 | 4 | 10 | 8 | 4 | 2 | 8 |
| 134 | 6 | 2 | 10 | 10 | 10 | 9 | 3 | 1 | 10 |
| 136 | 10 | 7 | 10 | 10 | 10 | 10 | 1 | 1 | 10 |
| 137 | 10 | 7 | 10 | 8 | 10 | 10 | 5 | 3 | 8 |
| 138 | 10 | 5 | 10 | 10 | 0 | 5 | 2 | 1 | 7 |
| 139 | 10 | 8 | 10 | 10 | 3 | 5 | 4 | 2 | 9 |
| 140 | 8 | 1 | 7 | 10 | 10 | 8 | 0 | 0 | 10 |
| 141 | 9 | 3 | 7 | 10 | 9 | 7 | 0 | 1 | 10 |
| 142 | 10 | 2 | 6 | 3 | 5 | 5 | 3 | 2 | 7 |
| 144 | 10 | 2 | 9 | 2 | 10 | 10 | 0 | 0 | 8 |
| 145 | 10 | 4 | 8 | 1 | 4 | 10 | 0 | 1 | 9 |

Note:
1) Blank represent untested data;
2) The application rate was 250 g/ha of active ingredient, with 450 kg/ha of adding water.

It is indicated from the experiment that the compound of the present invention generally have good weed control efficacy, especially for major grass weeds such as *echinochloa*, crab grass and foxtail, etc. and major broadleaf weeds such as Indian mallow, *rorippa indica* and *bidens bipinnata*, etc., which are widely occurred in corn, rice and wheat fields, and have excellent commercial value. Above all, it is noted that the compound of the invention have extremely high activity to broadleaf weeds, which are resistant to ALS inhibitor, like *rorippa indica*, flixweed, shepherd's purse, corn gromwell, cleavers and chickweed, etc.

With the application of ALS inhibitor herbicide (e.g. mesosulfuron, flucarbazone-sodium, pyroxsulam and chlorsulfuron, etc.) and ACCase inhibitor herbicide, herbicide resistant grass weeds in wheat field are increasing and bring about great challenge in China, Australia and Europe. Currently, most of the common herbicides exhibit the herbicidal activity by those two mechanisms. Thus seeking for new herbicides act through a different mechanism would bring new alternatives and has great social and commercial value. After screening, it is surprisingly to find that many compounds of the present invention have excellent control effect for *alopecurus* japonicas from Tianchang County of Anhui Province, China, which are both resistant to ALS inhibitor herbicide and ACCase inhibitor herbicides, and have good selectivity at the same time.

The seeds of *alopecurus japonicas*, flixweed, shepherd's purse, corn gromwell, chickweed, *beckmannia syzigachne*, and annual ryegrass and wheat seeds were put into a plastic pot loaded with soil, and then covered with 0.5-2 cm soil, the seeds were allowed to grow in good greenhouse environment. The test plants were treated at 4 leaf stage 2-3 weeks after sowing. The test compounds of the present invention were dissolved in acetone respectively, then added with methyl oleate emulsion and diluted by certain amount of water to certain concentration. The solution was sprayed to the plant with a sprayer. Then the plants were cultured for 4 weeks in greenhouse. The experiment result of weed controlling effect after 4 weeks was listed in table 2 and table 3.

TABLE 3

Test results of broadleaf weeds in part of wheat fields after applying 250 g/ha of the active substance.

| Compound ID | shepherd's purse | flixweed | corn gromwell | chickweed | wheat |
|---|---|---|---|---|---|
| 5 | 10 | 10 | 10 | 10 | 0 |
| 28 | 10 | 10 | 10 | 10 | 0 |
| 37 | 10 | 10 | 10 | 10 | 0 |
| 46 | 10 | 10 | 10 | 10 | 0 |
| 51 | 10 | 10 | 10 | 10 | 0 |
| 52 | 10 | 10 | 10 | 10 | 0 |
| 56 | 10 | 10 | 10 | 10 | 0 |
| 48 | 10 | 10 | 10 | 10 | 0 |
| 58 | 10 | 10 | 10 | 10 | 0 |
| 60 | 10 | 10 | 10 | 10 | 0 |
| 61 | 10 | 10 | 10 | 10 | 0 |
| 67 | 10 | 10 | 10 | 10 | 0 |
| 71 | 10 | 10 | 10 | 10 | 0 |
| 72 | 10 | 10 | 10 | 10 | 0 |
| 81 | 10 | 10 | 10 | 10 | 0 |
| 82 | 10 | 10 | 10 | 10 | 0 |
| 86 | 10 | 10 | 10 | 10 | 0 |
| 88 | 10 | 10 | 10 | 10 | 0 |
| 90 | 10 | 10 | 10 | 10 | 0 |
| 92 | 10 | 10 | 10 | 10 | 1 |
| 96 | 10 | 10 | 10 | 10 | 1 |
| 111 | 10 | 10 | 10 | 10 | 1 |
| 119 | 10 | 10 | 10 | 10 | 1 |
| 120 | 10 | 10 | 10 | 10 | 1 |
| 121 | 10 | 10 | 10 | 10 | 1 |
| 129 | 10 | 10 | 10 | 10 | 1 |
| 131 | 10 | 10 | 10 | 10 | 0 |
| 134 | 10 | 10 | 10 | 10 | 1 |
| 138 | 10 | 10 | 10 | 10 | 1 |
| 140 | 10 | 10 | 10 | 10 | 0 |
| 141 | 10 | 10 | 10 | 10 | 1 |
| 146 | 10 | 10 | 10 | 9 | 0 |
| 147 | 10 | 10 | 10 | 9 | 0 |
| 148 | 10 | 10 | 10 | 10 | 1 |

Note:
Weeds of *alopecurus japonicas* and *beckmannia syzigachne* are collected from Tianchang County of Anhui Province, China. They are tested to be resistant to labeled application rate of herbicides such as mesosulfuron and clodinafop, etc. Flixweed, shepherd's purse, corn gromwell and chickweed are collected from Jining of Shandong Province. They are tested to be resistant to labeled application rate of ALS inhibitor herbicides such as tribenuron-methyl and florasulam, etc.

Transplanted Rice Safety Evaluation and Weed Control Effect Evaluation in Rice Field:

Rice field soil was loaded into a 1/1,000,000 ha pot. The seeds of *echinochloa, scirpus juncoides, bidens tripartite* and *sagittaria trifolia* were sowed and gently covered with soil, then left to stand still in greenhouse in the state of 0.5-1 cm of water storage. The tuber of *sagittaria trifolia* was planted

TABLE 2

Test results of *alopecurus japonicas* in part of wheat fields after applying 250 g/ha of the active substance.

| Compound ID | Alopecurus japonicas | | | | Wheat | | | | |
|---|---|---|---|---|---|---|---|---|---|
| | 1 g/mu | 2 g/mu | 4 g/mu | 8 g/mu | 2 g/mu | 4 g/mu | 8 g/mu | 16 g/mu | 32 g/mu |
| 19 | 1 | 4 | 6 | 6 | 0 | 0 | 2 | 3 | 4 |
| 20 | 1 | 6 | 6 | 8 | 1 | 3 | 3 | 4 | 4 |
| 21 | 2 | 6 | 10 | 10 | 0 | 1 | 4 | 4 | 4 |
| 23 | 1 | 6 | 8 | 10 | 1 | 2 | 3 | 4 | 4 |
| 26 | 8 | 10 | 10 | 10 | 1 | 3 | 8 | 8 | 8 |
| 27 | 6 | 10 | 10 | 10 | 1 | 4 | 4 | 4 | 5 |
| 35 | 0 | 2 | 6 | 6 | 0 | 0 | 0 | 0 | 0 |
| 46 | 6 | 9 | 10 | 10 | 0 | 0 | 0 | 0 | 1 |
| 48 | 8 | 10 | 10 | 10 | 0 | 0 | 0 | 1 | 4 |
| 49 | 8 | 9 | 10 | 10 | 0 | 1 | 1 | 3 | 3 |
| 115 | 4 | 6 | 10 | 10 | 0 | 1 | 3 | 4 | 4 | in the next day or 2 days later. It was kept at 3-4 cm of water storage thereafter. The weeds were treated by dripping the WP or SC water diluents prepared according to the common preparation method of the compounds of the present invention with pipette homogeneously to achieve specified effective amount when *echinochloa, scirpus juncoides* and *bidens tripartite* reached 0.5 leaf stage and *sagittaria trifolia* reached the time point of primary leaf stage.

In addition, the rice field soil that loaded into the 1/1,000,000 ha pot was leveled to keep water storage at 3-4 cm depth. The 3 leaf stage rice (*japonica* rice) was transplanted at 3 cm of transplanting depth the next day. The compound of the present invention was treated by the same way after 5 days of transplantation.

The fertility condition of *echinochloa, scirpus juncoides, bidens tripartite* and *sagittaria trifolia* 14 days after the treatment of the compound of the invention and the fertility condition of rice 21 days after the treatment of the compound of the invention respectively with the naked eye. Evaluate the weed control effect with 1-10 activity standard level, which was presented in table 4.

TABLE 4

The experiment result of transplanted rice field (125 g/ha ai)

| Compound ID | Echinochloa | Scirpus juncoides | Sagittaria trifolia | Bidens tripartite | Rice |
|---|---|---|---|---|---|
| 1 | 10 | 10 | 9 | 8 | 0 |
| 23 | 10 | 10 | 10 | 10 | 0 |
| 25 | 9 | 10 | 10 | 8 | 0 |
| 35 | 8 | 10 | 9 | 9 | 0 |
| 37 | 10 | 10 | 10 | 10 | 2 |
| 54 | 8 | 9 | 9 | 9 | 2 |
| 65 | 9 | 9 | 9 | 8 | 3 |
| 68 | 10 | 9 | 10 | 10 | 1 |
| 71 | 10 | 10 | 10 | 8 | 0 |
| 77 | 10 | 10 | 10 | 9 | 1 |
| 81 | 10 | 10 | 10 | 10 | 1 |
| 92 | 10 | 10 | 10 | 9 | 0 |
| 128 | 10 | 10 | 8 | 6 | 1 |
| 129 | 10 | 10 | 10 | 10 | 2 |

Note:
*echinochloa, scirpus juncoides, sagittaria trifolia* and *bidens tripartite* seeds are all collected from Heilongjiang Province, China. The weeds are tested to be resistant to conventional application rate of pyrazosulfuron-ethyl.

At the same time, it is found after several tests that the compound of the present invention has good selectivity to many gramineae grass such as *zoysia japonica*, bermuda grass, tall fescue, bluegrass, ryegrass and seashore *paspalum* etc, and is able to control many important grass weeds and broadleaf weeds. The compound also shows excellent selectivity and commercial value in the tests on soybean, cotton, oil sunflower, potato, orchards and vegetables in different herbicide application methods.

What is claimed is:

1. A pyrazolone compound of formula I or a salt thereof:

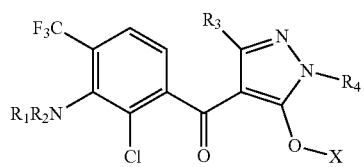

I wherein, $R_1R_2N$ represents substituted or unsubstituted 4-8 membered lactam group containing 0-2 heteroatoms selected from O, S and N; or,
$R_1$ and $R_2$ each represent hydrogen, $C_{1-8}$ alkyl, substituted alkyl containing 1-4 heteroatoms, alkenyl, alkynyl, substituted or unsubstituted $C_{1-4}$ acyl, unsubstituted $C_{3-6}$ cycloalkyl or $C_{3-6}$ cycloalkyl substituted by $C_{1-4}$ alkyl;
$R_3$ represents hydrogen, $C_{1-4}$ alkyl, alkenyl, alkynyl, unsubstituted $C_{3-6}$ cycloalkyl or $C_{3-6}$ cycloalkyl substituted by $C_{1-4}$ alkyl;
$R_4$ represents methyl, ethyl, n-propyl, isopropyl or cyclopropyl;
X represents hydrogen, —S(O)$_n$R$^6$, —R$^7$, —(C═O)R$^8$ or substituted or unsubstituted 3-8 membered heterocyclic group containing 1-4 heteroatoms, wherein, n represents 1, 2 or 3, R$^6$ represents substituted or unsubstituted alkyl or aryl, R$^7$ represents substituted or unsubstituted alkyl, aryl, alkyl acyl or aroyl, and R$^8$ represents alkoxy, aryloxy, substituted or unsubstituted alkyl or aryl, or substituted or unsubstituted 3-8 membered heterocyclic group containing 1-4 heteroatoms.

2. The pyrazolone compound or the salt thereof according to claim 1, which is characterized in that,
$R_1R_2N$ represents substituted or unsubstituted 4-8 membered lactam group containing 0-2 heteroatoms selected from O, S and N; or,
one of $R_1$ and $R_2$ represents $C_{1-4}$ acyl containing O, S or N, which is unsubstituted or substituted by halogen, and the other one represents hydrogen, $C_{1-8}$ alkyl and substituted alkyl containing 1-4 heteroatoms, alkenyl, alkynyl, unsubstituted $C_{3-6}$ cycloalkyl or $C_{3-6}$ cycloalkyl substituted by $C_{1-4}$ alkyl;
$R_3$ represents hydrogen, $C_{1-4}$ alkyl, alkenyl, alkynyl, unsubstituted $C_{3-6}$ cycloalkyl or $C_{3-6}$ cycloalkyl substituted by $C_{1-4}$ alkyl;
$R_4$ represents methyl, ethyl, n-propyl, isopropyl or cyclopropyl;
X represents hydrogen, —S(O)$_n$R$^6$, —R$^7$ or substituted or unsubstituted 3-8 membered heteroaryl containing 1-4 heteroatoms, wherein n represents 1, 2 or 3, R$^6$ represents substituted or unsubstituted alkyl or aryl, and R$^7$ represents substituted or unsubstituted alkyl, aryl, alkyl acyl or aroyl.

3. The pyrazolone compound or the salt thereof according to claim 1, which is characterized in that,
$R_1R_2N$ represents substituted or unsubstituted 4-8 membered lactam group containing 0-2 heteroatoms selected from O, S and N; or
one of $R_1$ and $R_2$ represents $C_{1-4}$ acyl containing O, S or N, which is unsubstituted or substituted by halogen, and the other one represents hydrogen, $C_{1-8}$ alkyl, substituted $C_{1-8}$ alkyl containing 1-4 heteroatoms, unsubstituted $C_{3-6}$ cycloalkyl or $C_{3-6}$ cycloalkyl substituted by $C_{1-4}$ alkyl;
$R_3$ represents hydrogen, methyl, ethyl or cyclopropyl;
$R_4$ represents methyl, ethyl or isopropyl;
X represents hydrogen, —SO$_2$R$^6$, or —(C═O)R$^8$, wherein R$^6$ represents substituted or unsubstituted alkyl or aryl, R$^8$ represents alkoxy, aryloxy, substituted or unsubstituted alkyl or aryl, or substituted or unsubstituted 3-8 membered heterocyclic group containing 1-4 heteroatoms.

4. The pyrazolone compound or the salt thereof according to claim 1, which is characterized in that,
$R_1R_2N$ represents a group selected from butyrolactam group, valeroalctam group, caprolactam group, oenantholactam group, piperazinone group, morpholinone group and thiomorpholinone group, each of which is unsubstituted or substituted on ring by one or more groups selected from fluorine, chlorine, methyl, ethyl, methoxyl and ethoxyl; or R₁ represents acetyl, fluoroacetyl, difluoroacetyl, trifluoroacetyl, methoxy acetyl, ethoxy acetyl, methoxy propionyl or ethoxy propionyl, R₂ represents hydrogen; cycloprropyl; or a group selected from methyl, ethyl, propyl, butyl and pentyl, each of which is unsubstituted or substituted by one or more groups selected from fluorine, methoxyl, ethyoxyl, propoxy, butoxy and methoxyethoxy;

R₃ represents hydrogen, methyl, ethyl or cyclopropyl;

R₄ represents methyl, ethyl or isopropyl;

X represents hydrogen, —SO₂R⁶, —(C═O)R⁸, wherein R⁶ represents substituted or unsubstituted alkyl or aryl, R⁸ represents alkoxy, aryloxy, substituted or unsubstituted alkyl or aryl, unsubstituted N-alkylpyrazolyl or N-alkylpyrazolyl substituted on ring by one or more groups selected from methyl, ethyl, methoxyl and ethoxyl.

5. A method for preparing the pyrazolone compound or the salt thereof according to claim 1, comprising the following steps:
(1) a compound of formula II is reacted with an excessive amount of compound R₁R₂NH to prepare a compound of formula III;
(2) the compound of formula III is reacted with compound X-A to obtain the compound of formula I;
wherein A represents halogen, methylsulfonyl or p-tosyl, and the reaction route is as follows:

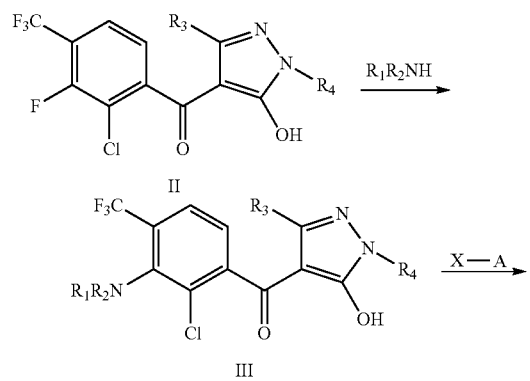

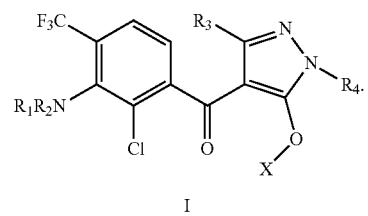

6. The method according to claim 5, which is characterized in that, said step (1) and step (2) are conducted in an aprotic solvent in the presence of a base; at a reaction temperature of −30° C. −180° C.

7. The method according to claim 6, which is characterized in that, said solvent is acetonitrile, diethyl ether, tetrahydrofuran, DMF or DMSO; said base is sodium hydroxide, potassium hydroxide, calcium hydroxide, sodium carbonate, potassium carbonate, sodium bicarbonate, potassium bicarbonate, triethylamine, DIPEA or DBU.

8. A herbicidal composition, which is characterized in that, it comprises a herbicidally effective amount of at least one pyrazolone compound or the salt thereof according to claim 1.

9. The herbicidal composition according to claim 8, which is characterized in that, it also comprises a preparation auxiliary.

10. A method for controlling a harmful plant, comprising a step of applying a herbicidally effective amount of at least one pyrazolone compound or the salt thereof according to claim 1 to the harmful plant or an area with the harmful plant.

11. A The pyrazolone compound or the salt thereof according to claim 1, wherein the compound is selected from

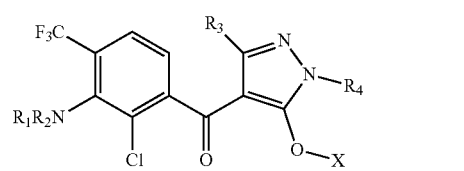

| compound ID | R₁R₂N- | R₃ | R₄ | X |
|---|---|---|---|---|
| 001 | 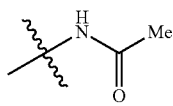 —NH₂ | Me | Me | H |
| 002 | ⸲N(H)–C(=O)Me | Me | Me | H |

-continued

| compound ID | R₁R₂N- | R₃ | R₄ | X |
|---|---|---|---|---|
| 003 | -NH-C(O)-CHF₂ | Me | Me | H |
| 004 | -N(Me)-Ac | Me | Me | H |
| 005 | -N(C(O)Me)-CH₂-CHF₂ | Me | Me | H |
| 006 | -N(C(O)Me)-CH₂CH₂CH₂-Me | Me | Me | H |
| 007 | -N(C(O)Me)-CH₂CH₂-O-Me | Me | Me | H |
| 008 | -N(C(O)Me)-CH₂CH₂CH₂-O-Me | Me | Me | H |
| 009 | -N(C(O)Me)-CH₂CH₂CH₂-O-Et | Me | Me | H |
| 010 | -N(C(O)Me)-CH₂CH₂CH₂-O-CH(Me)Me | Me | Me | H |
| 011 | -N(C(O)Me)-CH₂CH₂CH₂-O-Bu | Me | Me | H |
| 012 | -N(C(O)Me)-CH₂CH₂CH₂-O-CH₂CH(Me)-O-Me | Me | Me | H |

-continued

| compound ID | R₁R₂N- | R₃ | R₄ | X |
|---|---|---|---|---|
| 013 | N(Me)-C(O)-CH₂-O-Me | Me | Me | H |
| 014 | 2-oxopyrrolidin-1-yl | H | Me | H |
| 015 | 2-oxopyrrolidin-1-yl | H | Me | 5-ethoxy-1-methyl-1H-pyrazole-4-carbonyl |
| 016 | 2-oxopyrrolidin-1-yl | H | Me | 1,3-dimethyl-1H-pyrazole-4-carbonyl |
| 017 | 2-oxopyrrolidin-1-yl | H | Me | 1-methyl-1H-pyrazole-4-carbonyl |
| 018 | 2-oxopyrrolidin-1-yl | Me | Me | H |
| 019 | 2-oxopyrrolidin-1-yl | Me | Me | EtSO₂— |
| 020 | 2-oxopyrrolidin-1-yl | Me | Me | —C(O)OMe |
| 021 | 2-oxopyrrolidin-1-yl | Me | Me | 5-ethoxy-1-methyl-1H-pyrazole-4-carbonyl |

-continued

| compound ID | R₁R₂N- | R₃ | R₄ | X |
|---|---|---|---|---|
| 022 | pyrrolidin-2-one (N-linked) | Me | Me | 1-methyl-1H-pyrazol-4-yl carbonyl |
| 023 | pyrrolidin-2-one (N-linked) | Me | Me | 1,3-dimethyl-1H-pyrazol-4-yl carbonyl |
| 024 | 5-methoxypyrrolidin-2-one (N-linked) | Me | Me | H |
| 025 | pyrrolidin-2-one (N-linked) | cyclopropyl | Me | H |
| 026 | pyrrolidin-2-one (N-linked) | cyclopropyl | Me | 5-ethoxy-1-methyl-1H-pyrazol-4-yl carbonyl |
| 027 | pyrrolidin-2-one (N-linked) | cyclopropyl | Me | 1,3-dimethyl-1H-pyrazol-4-yl carbonyl |
| 028 | pyrrolidin-2-one (N-linked) | cyclopropyl | Me | 1-methyl-1H-pyrazol-4-yl carbonyl |
| 029 | piperidin-2-one (N-linked) | H | Me | H |

-continued
| compound ID | R₁R₂N- | R₃ | R₄ | X |
|---|---|---|---|---|
| 030 |  | H | Me | Ac— |
| 031 | 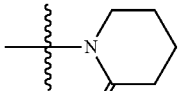 | H | Me | EtSO₂— |
| 032 |  | H | Me | 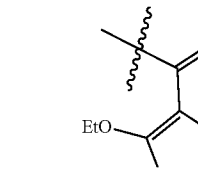 |
| 033 |  | H | Me | 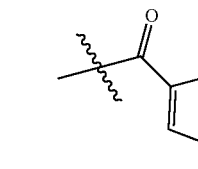 |
| 034 | 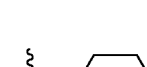 | H | Me | 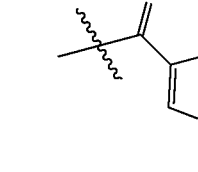 |
| 035 | 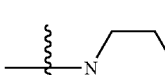 | Me | Me | H |
| 036 | 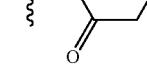 | Me | Me |  |
| 037 | 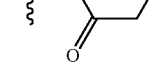 | Me | Me | 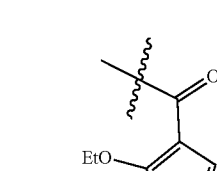 |

-continued

| compound ID | R₁R₂N- | R₃ | R₄ | X |
|---|---|---|---|---|
| 038 | 2-oxopiperidin-1-yl | Me | Me | 1,3-dimethyl-1H-pyrazol-4-yl carbonyl |
| 039 | 2-oxopiperidin-1-yl | Me | Me | 1-methyl-1H-pyrazol-4-yl carbonyl |
| 040 | 3-oxopiperazin-1-yl | Me | Me | H |
| 041 | 3-oxopiperazin-1-yl | Me | Me | 1-methyl-1H-pyrazol-4-yl carbonyl |
| 042 | 3-oxomorpholin-4-yl | Me | Me | H |
| 043 | 3-oxomorpholin-4-yl | Me | Me | 1-methyl-1H-pyrazol-4-yl carbonyl |
| 044 | 3-oxothiomorpholin-4-yl | Me | Me | H |
| 045 | 3-oxothiomorpholin-4-yl | Me | Me | 1-methyl-1H-pyrazol-4-yl carbonyl |

-continued

| compound ID | R₁R₂N- | R₃ | R₄ | X |
|---|---|---|---|---|
| 046 | piperidin-2-one (N-linked) | cyclopropyl | Me | H |
| 047 | piperidin-2-one (N-linked) | cyclopropyl | Me | -C(O)-(3-methyl-1-methyl-1H-pyrazol-4-yl) |
| 048 | piperidin-2-one (N-linked) | cyclopropyl | Me | -C(O)-(5-ethoxy-1-methyl-1H-pyrazol-4-yl) |
| 049 | piperidin-2-one (N-linked) | cyclopropyl | Me | -C(O)-(1-methyl-1H-pyrazol-4-yl) |
| 050 | azepan-2-one (N-linked) | H | Me | H |
| 051 | azepan-2-one (N-linked) | H | Me | -C(O)-(5-ethoxy-1-methyl-1H-pyrazol-4-yl) |
| 052 | azepan-2-one (N-linked) | H | Me | -C(O)-(3-methyl-1-methyl-1H-pyrazol-4-yl) |
| 053 | azepan-2-one (N-linked) | H | Me | -C(O)-(1-methyl-1H-pyrazol-4-yl) |

-continued

| compound ID | R₁R₂N- | R₃ | R₄ | X |
|---|---|---|---|---|
| 054 | azepan-2-one (N-linked) | Me | Me | H |
| 055 | azepan-2-one (N-linked) | Me | Me | -C(Me)₂-C(O)-O-Et |
| 056 | azepan-2-one (N-linked) | Me | Me | -C(Me)₂-C(O)-(5-EtO-1-Me-pyrazol-4-yl) |
| 057 | azepan-2-one (N-linked) | Me | Me | -C(Me)₂-C(O)-(1-Me-pyrazol-4-yl) |
| 058 | azepan-2-one (N-linked) | Me | Me | -C(Me)₂-C(O)-(1,3-diMe-pyrazol-4-yl) |
| 059 | azepan-2-one (N-linked) | cyclopropyl | Me | H |
| 060 | azepan-2-one (N-linked) | cyclopropyl | Me | -C(Me)₂-C(O)-(5-EtO-1-Me-pyrazol-4-yl) |
| 061 | azepan-2-one (N-linked) | cyclopropyl | Me | -C(Me)₂-C(O)-(1-Me-pyrazol-4-yl) |

-continued

| compound ID | R₁R₂N- | R₃ | R₄ | X |
|---|---|---|---|---|
| 062 | azepan-2-one (N-linked, 7-membered lactam) | cyclopropyl | Me | 1,3-dimethyl-1H-pyrazol-4-yl ketone |
| 096 | pyrrolidin-2-one (N-linked) | H | Et | H |
| 097 | pyrrolidin-2-one (N-linked) | H | Et | 1,3-dimethyl-1H-pyrazol-4-yl ketone |
| 098 | pyrrolidin-2-one (N-linked) | Me | Et | H |
| 099 | pyrrolidin-2-one (N-linked) | Me | Et | 1,3-dimethyl-1H-pyrazol-4-yl ketone |
| 100 | pyrrolidin-2-one (N-linked) | Et | Me | H |
| 101 | pyrrolidin-2-one (N-linked) | Et | Me | 1,3-dimethyl-1H-pyrazol-4-yl ketone |
| 102 | pyrrolidin-2-one (N-linked) | Et | Et | H |

-continued

| compound ID | R₁R₂N- | R₃ | R₄ | X |
|---|---|---|---|---|
| 103 | N-pyrrolidinone (2-oxopyrrolidin-1-yl) | Et | Et | 1,3-dimethyl-1H-pyrazol-4-yl carbonyl |
| 104 | 2-oxopyrrolidin-1-yl | cyclopropyl | Et | H |
| 105 | 2-oxopyrrolidin-1-yl | cyclopropyl | Et | 1,3-dimethyl-1H-pyrazol-4-yl carbonyl |
| 106 | 2-oxopiperidin-1-yl | H | Et | H |
| 107 | 2-oxopiperidin-1-yl | H | Et | 1,3-dimethyl-1H-pyrazol-4-yl carbonyl |
| 108 | 2-oxopiperidin-1-yl | Me | Et | H |
| 109 | 2-oxopiperidin-1-yl | Me | Et | 1,3-dimethyl-1H-pyrazol-4-yl carbonyl |
| 110 | 2-oxopiperidin-1-yl | Et | Me | H |

-continued

| compound ID | R₁R₂N- | R₃ | R₄ | X |
|---|---|---|---|---|
| 111 | piperidin-2-one (N-linked, 6-membered) | Et | Me | 1-methyl-3-methyl-1H-pyrazol-4-yl carbonyl |
| 112 | piperidin-2-one (N-linked, 6-membered) | Et | Et | H |
| 113 | piperidin-2-one (N-linked, 6-membered) | Et | Et | 1-methyl-3-methyl-1H-pyrazol-4-yl carbonyl |
| 114 | piperidin-2-one (N-linked, 6-membered) | cyclopropyl | Et | H |
| 115 | piperidin-2-one (N-linked, 6-membered) | cyclopropyl | Et | 1-methyl-3-methyl-1H-pyrazol-4-yl carbonyl |
| 116 | azepan-2-one (N-linked, 7-membered) | H | Et | H |
| 117 | azepan-2-one (N-linked, 7-membered) | H | Et | 1-methyl-3-methyl-1H-pyrazol-4-yl carbonyl |
| 118 | azepan-2-one (N-linked, 7-membered) | Me | Et | H |

-continued

| compound ID | R₁R₂N- | R₃ | R₄ | X |
|---|---|---|---|---|
| 119 | azepan-2-one (N-linked) | Me | Et | 1,3-dimethyl-1H-pyrazol-4-yl carbonyl |
| 120 | azepan-2-one (N-linked) | Et | Me | H |
| 121 | azepan-2-one (N-linked) | Et | Me | 1,3-dimethyl-1H-pyrazol-4-yl carbonyl |
| 122 | azepan-2-one (N-linked) | Et | Et | H |
| 123 | azepan-2-one (N-linked) | Et | Et | 1,3-dimethyl-1H-pyrazol-4-yl carbonyl |
| 124 | azepan-2-one (N-linked) | cyclopropyl | Et | H |
| 125 | azepan-2-one (N-linked) | cyclopropyl | Et | 1,3-dimethyl-1H-pyrazol-4-yl carbonyl |
| 146 | piperidin-2-one (N-linked) | cyclopropyl | CH₂CH₂Me | H |
| 147 | piperidin-2-one (N-linked) | cyclopropyl | CH(Me)Me | H |

-continued

| compound ID | R₁R₂N- | R₃ | R₄ | X |
|---|---|---|---|---|
| 148 | piperidin-2-one-N-yl | cyclopropyl | cyclopropyl | H. |

12. The method according to claim 6, wherein said step (1) and step (2) are both conducted at −5° C. −90° C.

13. The method according to claim 6, wherein the solvent is acetonitrile, tetrahydrofuran or DMF.

14. The method according to claim 6, wherein the base is NaH, triethylamine or potassium carbonate.

15. A method for controlling a harmful plant growing in a desirable crop, comprising a step of applying a herbicidally effective amount of at least one pyrazolone compound or the salt thereof according to claim 1 to the harmful plant or an area with the harmful plant.

16. The method according to claim 15, wherein the desirable crop is a genetically modified crop or a crop treated by a genome editing technique.

17. A method for controlling a harmful plant, comprising a step of applying a herbicidally effective amount of the herbicidal composition according to claim 8 to the harmful plant or an area with the harmful plant.

18. A method for controlling a harmful plant growing in a desirable crop, comprising a step of applying a herbicidally effective amount the herbicidal composition according to claim 8 to the harmful plant or an area with the harmful plant.

19. The method according to claim 18, wherein the desirable crop is a genetically modified crop or a crop treated by a genome editing technique.

* * * * *